(12) United States Patent
Shoji et al.

(10) Patent No.: US 8,507,564 B2
(45) Date of Patent: Aug. 13, 2013

(54) METHOD FOR SELECTING PERFUME INGREDIENT, METHOD FOR FORMULATING FRAGRANCE, AND PREFERENCE-ENHANCING AGENT

(75) Inventors: Ken Shoji, Yokohama (JP); Sumie Taguchi, Yokohama (JP); Yushi Terajima, Yokohama (JP); Katsuo Hashimoto, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 679 days.

(21) Appl. No.: 11/997,770

(22) PCT Filed: Aug. 1, 2006

(86) PCT No.: PCT/JP2006/315212
§ 371 (c)(1),
(2), (4) Date: Feb. 15, 2008

(87) PCT Pub. No.: WO2007/015481
PCT Pub. Date: Feb. 8, 2007

(65) Prior Publication Data
US 2010/0168253 A1  Jul. 1, 2010

(30) Foreign Application Priority Data

| | | |
|---|---|---|
| Aug. 4, 2005 | (JP) | 2005-227120 |
| Mar. 20, 2006 | (JP) | 2006-076721 |
| Mar. 20, 2006 | (JP) | 2006-076722 |
| Mar. 20, 2006 | (JP) | 2006-076723 |

(51) Int. Cl.
*C11B 9/00* (2006.01)
*A61Q 13/00* (2006.01)
*C11D 3/50* (2006.01)
*C11D 9/44* (2006.01)

(52) U.S. Cl.
USPC ............... 514/783; 514/772; 514/785; 512/5; 512/26; 73/23.34; 510/107; 510/101

(58) Field of Classification Search
USPC ................. 514/783, 772, 785; 512/5, 27, 21, 512/11, 26; 510/103, 107, 101; 72/23.34
See application file for complete search history.

(56) References Cited

U.S. PATENT DOCUMENTS

| | | |
|---|---|---|
| 5,104,851 A | 4/1992 | Fujikura et al. |
| 5,190,747 A * | 3/1993 | Sekiguchi et al. .............. 424/56 |

(Continued)

FOREIGN PATENT DOCUMENTS

| | | |
|---|---|---|
| EP | 1254651 | 11/2002 |
| EP | 1661973 | 5/2006 |

(Continued)

OTHER PUBLICATIONS

Leslie Everton Brice (Dec. 29, 2005) Company reaches out to your nose :[Home Edition]. The Atlanta Journal—Constitution, p. XJQ.5. [Downloaded Dec. 27, 2010] [Retrieved from Business Dateline (Document ID: 950526271)] [Retrieved from internet <URL: http://proquest.umi.com/pqdweb?did=950526271&sid=1&Fmt=3 &clientid=19649&RQT=309&VName=PQD>] Brice, (5 pages, including 2 citation pages).*

(Continued)

*Primary Examiner* — Jason M Sims
*Assistant Examiner* — Miriam A Levin
(74) *Attorney, Agent, or Firm* — Rankin, Hill & Clark LLP

(57) ABSTRACT

Methods for enhancing a preference for a product by repetitive use. The method involves formulating a perfume composition into a product, the perfume composition including (I) allyl caproate and (II) ambroxan or geranium oil.

9 Claims, 8 Drawing Sheets

(56) References Cited

U.S. PATENT DOCUMENTS

| | | | |
|---|---|---|---|
| 5,780,404 A * | 7/1998 | Bacon et al. | 510/101 |
| 6,463,786 B1 | 10/2002 | Behan et al. | |
| 6,858,574 B2 * | 2/2005 | Yang et al. | 512/1 |
| 7,016,882 B2 * | 3/2006 | Afeyan et al. | 706/13 |
| 2002/0103094 A1 * | 8/2002 | Masschelein et al. | 510/276 |
| 2004/0091595 A1 * | 5/2004 | Dewis et al. | 426/534 |
| 2004/0127463 A1 | 7/2004 | Trinh et al. | |
| 2004/0242452 A1 * | 12/2004 | Shoji et al. | 512/1 |
| 2005/0129721 A1 | 6/2005 | Ishida et al. | |
| 2005/0158269 A1 | 7/2005 | Simonet | |
| 2006/0159639 A1 * | 7/2006 | Ogura et al. | 424/65 |
| 2006/0165863 A1 * | 7/2006 | Behan et al. | 426/534 |
| 2006/0207037 A1 * | 9/2006 | Fadel et al. | 8/406 |
| 2008/0008665 A1 * | 1/2008 | Ramji et al. | 424/48 |

FOREIGN PATENT DOCUMENTS

| | | |
|---|---|---|
| JP | 05-310944 | 11/1993 |
| JP | 2001-174450 | 6/2001 |
| JP | 2003-081804 | 3/2003 |
| JP | 2003-113392 | 4/2003 |
| WO | 2005/041918 | 5/2005 |
| WO | WO 2005046632 A2 * | 5/2005 |

OTHER PUBLICATIONS

Hilda Butler, ed., Poucher's Perfumes, Cosmetics and Soaps, 10th ed., Chapter 24 "Perfume and the manufacture of consumer products," Kluwer Academic Publishers (2000), pp. 717, 728 (4 pages).*

W.A. Poucher, Poucher's Perfumes, Cosmetics and Soaps, 9th ed., vol. 2, Chapter 4, "Odour Classification and Fixation," Chapman & Hall, New York (1993), pp. 46-67 (13 pages).*

The Good Scents Company, Hydroxycitronellal [Downloaded Jan. 3, 2011] [Retrieved from internet <URL: http://www.thegoodscentscompany.com/data/rw1004281.html>], (7 pages).*

The Good Scents Company, musk gx 50% in dep [Downloaded Jan. 3, 2011] [Retrieved from internet <URL: http://www.thegoodscentscompany.com/data/rw100751.html?], (15 pages).*

The Good Scents Company, armoise oil [Downloaded Jan. 3, 2011] [Retrieved from internet <URL: http://www.thegoodscentscompany.com/data/es1024711.html>], (5 pages).*

Essential Oils, Esoteric Oils, Wormwood oil (Artemisia absinthium) [Downloaded Jan. 3, 2011] [Retrieved from internet <URL: http://www.essentialoils.co.za/essential-oils/wormwood.html>], (6 pages).*

The Good Scents Company, Allyl Caproate [Downloaded Sep. 7, 2011] [Retrieved from internet <URL: http://web.archive.org/web/20041107204138/http://www.thegoodscentscompany.com/data/rw1000731.html >] (from website last updated Jun. 10, 2004), 1 page.*

The Good Scents Company, Allyl Caproate [Downloaded Sep. 7, 2011] [Retrieved from internet <URLhttp://web.archive.org/web/20051027095601/http://www.thegoodscentscompany.com/data/rw1000731.html >] (from website last updated May 24, 2005), 2 pages.*

International Preliminary Report on Patentability for PCT/JP2006/315212 (Feb. 5, 2008) [Retrieved from WIPO website], 6 pages.*

Supplementary Partial European Search Report dated Oct. 16, 2008 for European Application No. 06782090, two pages.

European Search Report for corresponding EP 09172820 mailed Dec. 8, 2009, five pages.

Japanese Office Action 2006-076722 issued Jan. 6, 2012 corresponding to JP2005/227120, seventeen pages.

Explanation (in English) of the Relevance of Japanese Office Action 2006-076722 issued Jan. 6, 2012, 1 page.

Partial English Translation of JP 2003-081804 published Mar. 19, 2003; three pages.

Partial English Translation of JP 2003-113392 published Apr. 18, 2003; two pages.

* cited by examiner

# US 8,507,564 B2

METHOD FOR SELECTING PERFUME INGREDIENT, METHOD FOR FORMULATING FRAGRANCE, AND PREFERENCE-ENHANCING AGENT

RELATED APPLICATIONS

The present application claims the priorities of Japanese Patent Application No. 2005-227120 filed on Aug. 4, 2005 and Japanese Patent Application Nos. 2006-76721, 2006-76722, and 2006-76723 filed on Mar. 20, 2006. The contents thereof are incorporated herein.

FIELD OF THE INVENTION

The present invention relates to a method for selecting a perfume ingredient and a method for formulating a fragrance. Particularly, the present invention relates to the development of a method for selecting a perfume ingredient that enhances a preference therefor by continuous use.

BACKGROUND OF THE INVENTION

In a social psychological field, a so-called mere exposure effect has heretofore been known, in which repetitive exposures to a subject enhance a preference for the subject. More specifically, it has been reported that: (1) repetitive exposures to a stimulus form a favorable attitude to the stimulus; (2) the more the number of exposures increases, the more the liking increases; and (3) stimuli are classified into those easily increasing the liking and those not easily increasing the liking. These findings have been demonstrated in people photographs (visual sense), melodies (auditory sense), sweetness and bitterness (gustatory sense), and so on. Nevertheless, no cases of scientific testing on the relationship between a fragrance (olfactory sense) and repetitive stimuli have been reported. Specifically, the finding has not yet been obtained that a preference for a fragrance is enhanced by continuous use.

On the other hand, cosmetics such as makeup or toiletry products such as shampoos are used almost every day. It has been desired that a fragrance of choice for consumers should be imparted to those products. However, under present circumstances, any study as to a fragrance imparted to these various products has not been conducted so far on change in preference for the fragrance when the products are repetitively used. If a fragrance that enhances a preference therefor by continuous use can be selected and imparted to these cosmetics or toiletry products, the continued purchase of the products by consumers can be expected.

A more specific description will be given to a hair cleanser. Even a hair cleanser, which offers a cleansing power, foaming, use texture, and use texture after hair drying sufficiently satisfactory to consumers in trial use at stores or in use immediately after purchase, brings about a phenomenon in which consumers' high intentions to continuously use the product are not obtained, even though the physical functions of the product are not reduced in daily use. This may be due to a phenomenon in which the consumers are bored to the product due to the continuous use or because consumer mentality is activated which requires more highly satisfactory product functions. Under present circumstances, for example, consumers buy many new different products and, as a result, feel a sense of satisfaction in using the hair cleansers. Thus, it was difficult to keep a high sense of satisfaction when the same products were continuously used.

Thus, if a hair cleanser that improves use texture thereof by continuous use can be provided, the continuous purchase of the same products by consumers can probably be expected.

DISCLOSURE OF THE INVENTION

Problem to be Solved by the Invention

The present invention has been conducted in consideration of the problems of the prior art as described above. A first object thereof is to provide a method for selecting a perfume ingredient that can enhance a preference therefor by continuous use from among arbitrary perfume ingredients.

A second object of the present invention is to provide a perfume composition that can give a high preference therefor and enhance the preference by continuous use.

A third object of the present invention is to provide a hair cleanser that can offer excellent use texture and improve the use texture by continuous use.

Means to Solve the Problem

The present inventors have conducted diligent studies in consideration of the objects and have consequently found that only a perfume ingredient that enhances a preference therefor by continuous use can be selected by conducting a particular evaluation on arbitrary perfume ingredients and using this evaluation result as an indicator. Moreover, the present inventors have found that a preference for a perfume composition comprising plural perfume ingredients can also be enhanced by continuous use thereof by conducting a particular evaluation on the overall fragrance note of the composition and formulating a fragrance with this evaluation result as an indicator. Furthermore, the present inventors have found that, particularly, a perfume composition that can give a high preference therefor in first use and enhance the preference by continuous use can be obtained by using particular kinds of perfume ingredients such as allyl caproate and other particular kinds of perfume ingredient in combination. Moreover, the present inventors have found that a hair cleanser that can offer excellent use texture and improve the use texture by continuous use can be obtained by further formulating a particular ingredient typified by allyl caproate into a hair cleanser blended with an amphoteric surfactant, a cationic polymer, and an N-acyl-N-methyltaurine-based anionic surfactant. Consequently, the present inventors have completed the present invention.

Specifically, a method for selecting a perfume ingredient according to the present invention is characterized by comprising; conducting the following evaluation (X) on arbitrary perfume ingredients, and making a selection with the evaluation result as an indicator:

(X) an evaluation of a preference for a fragrance on first exposure and an evaluation of a preference for the fragrance after two or more exposures.

Moreover, a method for selecting a perfume ingredient according to the present invention is characterized by comprising; selecting a perfume ingredient that satisfies the following condition (x) from among arbitrary perfume ingredients:

(x) a preference for a fragrance after two or more exposures is evaluated as being increased as compared with a preference for the fragrance on first exposure.

Moreover, a method for selecting a perfume ingredient according to the present invention is characterized by comprising; conducting the following evaluation (A) and/or (B)

on arbitrary perfume ingredients, and making a selection with the evaluation result as an indicator:
(A) an evaluation of an impression of the "density" of a fragrance on first exposure and an evaluation of an impression of the "density" of the fragrance after two or more exposures; and
(B) an evaluation of an impression of the "cheerfulness" of a fragrance on first exposure and an evaluation of an impression of the "cheerfulness" of the fragrance after two or more exposures.

Moreover, a method for selecting a perfume ingredient according to the present invention is characterized by comprising; selecting a perfume ingredient that satisfies the following condition (a) and/or (b) from among arbitrary perfume ingredients:
(a) an impression of the "density" of a fragrance after two or more exposures is evaluated as being reduced as compared with an impression of the "density" of the fragrance on first exposure; and
(b) an impression of the "cheerfulness" of a fragrance after two or more exposures is evaluated as being increased as compared with an impression of the "cheerfulness" of the fragrance on first exposure.

Moreover, for the method for selecting a perfume ingredient according to the present invention, it is preferred that a perfume ingredient that further satisfies the following condition (c) should be selected:
(c) the impression of the "density" of the fragrance on first exposure is evaluated on a scale of 1 to 7 and rated 4 or higher.

Moreover, a perfume composition according to the present invention is characterized by comprising a perfume ingredient selected by the method for selecting a perfume ingredient.

Moreover, a method for formulating a fragrance according to the present invention is characterized by comprising; conducting the following evaluation (X) on the overall fragrance note of a perfume composition, and formulating a fragrance with the evaluation result as an indicator:
(X) an evaluation of a preference for a fragrance on first exposure and an evaluation of a preference for the fragrance after two or more exposures.

Moreover, a method for formulating a fragrance according to the present invention is characterized by comprising; formulating a fragrance so that the overall fragrance note of a perfume composition satisfies the following condition (x):
(x) a preference for a fragrance after two or more exposures is evaluated as being increased as compared with a preference for the fragrance on first exposure.

Moreover, a method for formulating a fragrance according to the present invention is characterized by comprising; conducting the following evaluation (A) and/or (B) on the overall fragrance note of a perfume composition, and formulating a fragrance with the evaluation result as an indicator:
(A) an evaluation of an impression of the "density" of a fragrance on first exposure and an evaluation of an impression of the "density" of the fragrance after two or more exposures; and
(B) an evaluation of an impression of the "cheerfulness" of a fragrance on first exposure and an evaluation of an impression of the "cheerfulness" of the fragrance after two or more exposures.

Moreover, a method for formulating a fragrance according to the present invention is characterized by comprising; formulating a fragrance so that the overall fragrance note of a perfume composition satisfies the following condition (a) and/or (b):
(a) an impression of the "density" of a fragrance after two or more exposures is evaluated as being reduced as compared with an impression of the "density" of the fragrance on first exposure; and
(b) an impression of the "cheerfulness" of a fragrance after two or more exposures is evaluated as being increased as compared with an impression of the "cheerfulness" of the fragrance on first exposure.

Moreover, for the method for formulating a fragrance, it is preferred that the fragrance should be formulated so that the overall fragrance note of the perfume composition further satisfies the following condition (c):
(c) the impression of the "density" of the fragrance on first exposure is evaluated on a scale of 1 to 7 and rated 4 or higher.

Moreover, a perfume composition according to the present invention is characterized in that a fragrance thereof is formulated by the method for formulating a fragrance of a perfume composition.

Moreover, a preference-enhancing agent according to the present invention is characterized by consisting of the perfume composition.

Moreover, a cosmetic according to the present invention is characterized by comprising the perfume composition.

Moreover, a method for enhancing a preference for a product by repetitive use according to the present invention is characterized by comprising; formulating the perfume composition into a product.

Moreover, a perfume composition according to the present invention is characterized by comprising one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Moreover, the perfume composition according to the present invention is characterized by comprising (I) one or more selected from the group consisting of allyl caproate, vanillin, octylaldehyde, nutmeg oil, and jasmine oil and (II) one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil.

Moreover, an preference-enhancing agent according to the present invention is characterized by comprising one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Moreover the preference-enhancing agent according to the present invention is characterized by comprising (I) one or more selected from the group consisting of allyl caproate, vanillin, octylaldehyde, nutmeg oil, and jasmine oil and (II) one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil.

Moreover, a cosmetic according to the present invention is characterized by comprising one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Moreover, the cosmetic according to the present invention is characterized by comprising (I) one or more selected from the group consisting of allyl caproate, vanillin, octylaldehyde, nutmeg oil, and jasmine oil and (II) one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil.

A hair cleanser according to the present invention is characterized by comprising (i) an amphoteric surfactant, (ii) a cationic polymer, (iii) an N-acyl-N-methyltaurine-based anionic surfactant, and (iv) one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Moreover, for the hair cleanser, it is preferred that the ingredient (iv) should be one or more selected from the group consisting of allyl caproate, vanillin, octylaldehyde, nutmeg oil, and jasmine oil.

Moreover, a method for enhancing a preference for a product by repetitive use according to the present invention is characterized by comprising; formulating the perfume composition comprising one or more selected from the group of the particular perfume ingredients into a product.

Effect of the Invention

According to the method for selecting a perfume ingredient according to the present invention, only a perfume ingredient that enhances a preference therefor by continuous use can be selected by conducting a particular evaluation on arbitrary perfume ingredients and using this evaluation result as an indicator. Moreover, according to the method for formulating a fragrance according to the present invention, a fragrance that enhances a preference for a perfume composition by continuous use can be formulated by conducting a particular evaluation on the overall fragrance note of the composition and formulating a fragrance with this evaluation result as an indicator.

The perfume composition according to the present invention can give a high preference therefor in first use, that is, a favorable first impression of a fragrance, and further enhance the preference by continuous use.

Moreover, the hair cleanser according to the present invention can offer excellent use texture and improve the use texture by continuous use, by further formulating a particular ingredient typified by allyl caproate into a hair cleanser blended with an amphoteric surfactant, a cationic polymer, and an N-acyl-N-methyltaurine-based anionic surfactant.

BEST MODE FOR CARRYING OUT THE INVENTION

Figure 1:
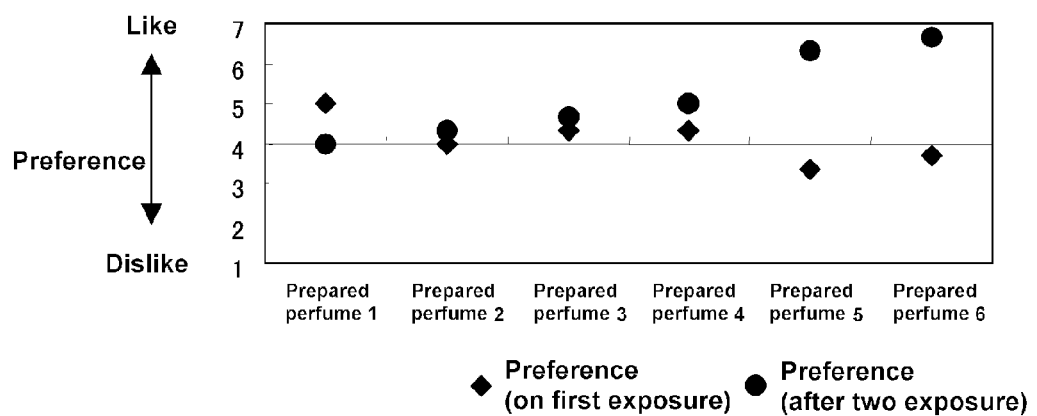
FIG. 1 shows evaluation results of preferences for six prepared perfumes on first exposure and after two exposures (on first exposure: an evaluation under the condition in which panelists do not take a smell at the prepared perfumes beforehand; after two exposures: an evaluation under the condition in which panelists take a smell at the prepared perfumes in advance)

Hereinafter, preferable embodiments of the present invention will be described. However, the present invention is not limited to them. In the present invention, a perfume ingredient refers to a single ingredient (including essential oil) as a perfume material, and a perfume composition refers to a mixture containing two or more of the perfume ingredients.

Method for Selecting Perfume Ingredient

A method for selecting a perfume ingredient according to the present invention is characterized by comprising; conducting the following evaluation (X) on arbitrary perfume ingredients, and making a selection with the evaluation result as an indicator:

(X) an evaluation of a preference for a fragrance on first exposure and an evaluation of a preference for the fragrance after two or more exposures.

Hereinafter, the evaluation (X) will be described.

The preference evaluation (X) is an evaluation of whether a test subject can have a good feeling toward the fragrances of arbitrary perfume ingredients. For example, evaluation values of preferences for the fragrances of arbitrary perfume ingredients can be determined by use of an evaluation test shown below.

Preference evaluation: 10 or more panelists rate a "preference" for the target perfume ingredient on a scale of 1 to 7 according to evaluation criteria below. In this context, an average value obtained by dividing, by the number of the panelists, the total sum of the scores given by the panelists is used as an evaluation value of the "preference".

| <Evaluation criteria> | |
|---|---|
| Very like | 7 |
| Like | 6 |
| Moderately like | 5 |
| Neither like nor dislike | 4 |
| Moderately dislike | 3 |
| Dislike | 2 |
| Very dislike | 1 |

In the evaluation (X), an evaluation value of an impression of the "preference" is determined for the arbitrary perfume ingredients under each condition of "on first exposure" and "after two or more exposures". In this context, the evaluation "on first exposure" means that the "preference" evaluation is conducted under the condition in which the test subject is exposed to the target perfume ingredient for the first time at the time of the test, that is, under the condition in which the test subject does not take a smell at the target perfume ingredient beforehand.

Alternatively, the evaluation "after two or more exposures" means that the "preference" evaluation is conducted under the condition in which the test subject is exposed once or more times before the test to the target perfume ingredient, that is, under the condition in which the test subject takes a smell at the target perfume ingredient once or more times in advance. In this context, it is preferred that the test subject should take a smell at the target perfume ingredient before the test without cognition. Specifically, for the "preference" evaluation "after two or more exposures", it is preferred that the test subject should take a smell at the target perfume ingredient once or more times in advance without informing the identity of the perfume ingredient and then take a smell at the same target perfume ingredient another time, followed by an evaluation of a "preference" of a fragrance. Alternatively, even if the test subject recognizes that he or she has already taken a smell at the target perfume ingredient, it is preferred that the evaluations "on first exposure" and "after two or more exposures" should be conducted discontinuously (e.g., a period during which the test subject takes a smell at the perfume ingredient without conducting an evaluation is provided between the preference evaluations "on first exposure" and "after two or more exposures").

In this context, for example, when the evaluations "on first exposure" and "after two or more exposures" are continuously conducted under the condition in which the test subject has already been informed about the identity of the target perfume ingredient, the test subject focuses his or her attention only on a preference for a fragrance. Therefore, a proper evaluation cannot be done. In this case, change in preferences "on first exposure" and "after two or more exposures" may not be seen. Therefore, even if the same test subject continuously conducts "preference evaluations" on arbitrary perfume ingredients, a perfume ingredient that enhances a preference therefor by continuous use cannot preferably be selected.

In a method for selecting a perfume ingredient according to the present invention, a perfume ingredient that satisfies the following condition (x) can be selected as a perfume ingredient that enhances a preference therefor by continuous use, as a result of conducting the evaluation (X) on arbitrary perfume ingredients:

(x) a preference for a fragrance after two or more exposures is evaluated as being increased as compared with a preference for the fragrance on first exposure.

For the condition (x), it is required that an evaluation value of a "preference" for a fragrance after two or more exposures should be larger than an evaluation value of a preference for the fragrance on first exposure. The degree of this increase is not particularly limited and may be, for example, an increase by 0.1 or more in the evaluation on a scale of 1 to 7.

Moreover, a method for selecting a perfume ingredient according to the present invention is characterized by comprising conducting the following evaluation (A) and/or (B) on arbitrary perfume ingredients and making a selection with the evaluation result as an indicator:

(A) an evaluation of an impression of the "density" of a fragrance on first exposure and an evaluation of an impression of the "density" of the fragrance after two or more exposures; and (B) an evaluation of an impression of the "cheerfulness" of a fragrance on first exposure and an evaluation of an impression of the "cheerfulness" of the fragrance after two or more exposures.

Hereinafter, the evaluations (A) and (B) will be described.

In the evaluations (A) and (B), each evaluation item such as the "density" and the "cheerfulness" specified as an evaluation of an impression on the perfume ingredients has been described in Japanese Patent Publication No. 2001-174450 as an appropriate evaluation item in an olfactory sense evaluation. In the evaluations (A) and (B), for example, an evaluation value of an impression of the "density" or the "cheerfulness" of a fragrance can be determined by use of an evaluation test shown below.

"Density": 10 or more panelists take a smell at the target perfume ingredient and two or more comparative perfume ingredients and rate an impression of the "density" of the target perfume ingredient on a scale of 1 to 7 according to evaluation criteria below by comparing it with that of the comparative perfume ingredients. In this context, perfume compositions in each evaluation phase (e.g., 1.0 and 5.0) are prepared for use as the comparative perfume ingredients with respect to a "density" evaluation of calone rated 3.0 and a "density" evaluation of geranium oil rated 5.5. In this context, an average value obtained by dividing, by the number of the panelists, the total sum of the scores given by the panelists is used as an evaluation value of the impression of "density".

| <Evaluation criteria> | |
|---|---|
| Very perceivable | 7 |
| Perceivable | 6 |
| Moderately perceivable | 5 |
| Neither perceivable nor unperceivable | 4 |
| Less perceivable | 3 |
| Unperceivable | 2 |
| Completely unperceivable | 1 |

"Cheerfulness": 10 or more panelists take a smell at the target perfume ingredient and two or more comparative perfume ingredients and rate an impression of the "cheerfulness" of the target perfume ingredient on a scale of 1 to 7 according to the evaluation criteria above by comparing it with that of the comparative perfume ingredients. In this context, perfume compositions in each evaluation phase (e.g., 2.0 and 6.0) are prepared for use as the comparative perfume ingredients with respect to a "cheerfulness" evaluation of patchouli oil rated 2.0 and a "cheerfulness" evaluation of grapefruit oil rated 6.0. In this context, an average value obtained by dividing, by the number of the panelists, the total sum of the scores given by the panelists is used as an evaluation value of the impression of "cheerfulness".

Moreover, in the evaluations (A) and (B), the evaluation "on first exposure" means that the impression evaluation is conducted under the condition in which the test subject is exposed to the target perfume ingredient for the first time at the time of the test, that is, under the condition in which the test subject does not take a smell at the target perfume ingredient beforehand. Alternatively, the evaluation under the condition of "after two or more exposures" means that the impression evaluation is conducted under the condition in which the test subject is exposed once or more times before the test to the target test subject, that is, under the condition in which the test subject takes a smell at the target perfume ingredient once or more times in advance. In this context, it is preferred that the test subject should take a smell at the target perfume ingredient before the test without cognition. Specifically, for the impression evaluation "after two or more exposures", it is preferred that the test subject should take a smell at the target perfume ingredient once or more times in advance without informing the identity of the perfume ingredient and then take a smell at the same target perfume ingredient another time, followed by an evaluation of an impression of a fragrance. Alternatively, even if the test subject recognizes that he or she has already taken a smell at the target perfume ingredient, it is preferred that the evaluations of impressions of a fragrance "on first exposure" and "after two or more exposures" should be conducted discontinuously.

In a method for selecting a perfume ingredient according to the present invention, a perfume ingredient that satisfies the following condition (a) and/or (b) can be selected as a perfume ingredient that enhances a preference therefor by continuous use, as a result of conducting the evaluation (A) and/or (B) on arbitrary perfume ingredients:

(a) an impression of the "density" of a fragrance after two or more exposures is evaluated as being reduced as compared with an impression of the "density" of the fragrance on first exposure; and (b) an impression of the "cheerfulness" of a fragrance after two or more exposures is evaluated as being increased as compared with an impression of the "cheerfulness" of the fragrance on first exposure.

For the condition (a), it is required that an evaluation value of an impression of the "density" of a fragrance after two or more exposures should be smaller than an evaluation value of an impression of the "density" of the fragrance on first exposure. The degree of this reduction is not particularly limited and may be, for example, a reduction by 0.1 or more in the evaluation on a scale of 1 to 7. Alternatively, for the condition (b), it is required that an evaluation value of an impression of the "cheerfulness" of a fragrance after two or more exposures should be larger than an evaluation value of an impression of the "cheerfulness" of the fragrance on first exposure. Likewise, the degree of this increase is not particularly limited and may be, for example, an increase by 0.1 or more in the evaluation on a scale of 1 to 7.

For the method for selecting a perfume ingredient according to the present invention, it is required that the perfume ingredient should satisfy either the condition (a) or (b). Particularly, it is preferred that the perfume ingredient should satisfy both of the conditions (a) and (b). When a perfume ingredient that satisfies neither the condition (a) nor (b) is selected, the perfume ingredient may not enhance a preference therefor even by continuous use.

Moreover, for the method for selecting a perfume ingredient according to the present invention, it is preferred that a perfume ingredient that further satisfies the following condition (c) should be selected:

(c) the impression of the "density" of the fragrance on first exposure is evaluated on a scale of 1 to 7 and rated 4 or higher.

In the condition (c), the impression of the "density" of the fragrance on first exposure can be evaluated by the evaluation (A) above. In the method for selecting a perfume ingredient according to the present invention, when a perfume ingredient whose impression of the "density" of the fragrance on first exposure is rated 4 or higher is selected, the perfume ingredient can significantly enhance a preference therefor by continuous use. On the other hand, a perfume ingredient whose impression of the "density" of the fragrance on first exposure is rated less than 4 is selected, the perfume ingredient may hardly enhance a preference therefor even by continuous use.

In the method for selecting a perfume ingredient according to the present invention, a manner in which the test subject takes a smell at a fragrance is not particularly limited. Specifically, for example, a vial (2.5 cm in diameter, 5 cm in height) containing cotton of 2 cm square is prepared. To the cotton, 0.05 ml of an alcohol solution of a perfume ingredient is applied. The cotton is left for 30 minutes to volatilize the alcohol. The test subject takes a smell at this cotton.

Examples of a perfume ingredient selected by the method for selecting a perfume ingredient described above, that is, a perfume ingredient that can enhance a preference therefor by continuous use include galaxolide (10%), ambroxan (1%), manzanate (1%), grapefruit oil (10%), marjoram oil (5%), cinnamon oil (0.5%), aurantiol (10%), tomato leaf extract (0.5%), spearmint oil (3%), clove oil (1%), chamomile oil (1%), pepper oil (0.5%), Triplal (0.1%), Yuzu citron (Citrus junos) oil (10%), octylaldehyde (0.1%), vanillin (5%), jasmine oil (1%), bergamot oil (10%), armoise oil (0.5%), strawberry extract (10%), geranium oil (5%), lime oil (10%), nutmeg oil (0.5%), and allyl caproate (10%).

Moreover, the perfume ingredients selected by the method for selecting a perfume ingredient described above are formulated into a perfume composition to prepare a perfume composition comprising two or more of the perfume ingredients. As a result, the effect of enhancing a preference for the perfume composition by continuous use can be expected in the perfume composition. Such a perfume composition is also incorporated in the present invention. To formulate the perfume composition, a perfume ingredient selected according to the present invention by usual means for formulating a fragrance is mixed with other perfume ingredients at appropriate proportions and formulated into a perfume composition with a preferable fragrance by formulating the fragrance. Such a perfume composition may be used. It is particularly preferred that two or more of the perfume ingredients selected according to the present invention should be mixed into the perfume composition for use.

Method for Formulating Fragrance

Moreover, the overall fragrance of a perfume composition comprising two or more of the perfume ingredients can be formulated by use of the method for evaluating a perfume ingredient described above to thereby obtain a perfume composition that can enhance a preference therefor by continuous use. Specifically, a fragrance of a perfume composition that enhances a preference therefor by continuous use can be formulated by conducting the evaluation (X) or the evaluations (A) and (B) above on the overall fragrance note of the perfume composition and formulating a fragrance with the evaluation result as an indicator.

Moreover, a perfume composition whose fragrance is formulated by the method for formulating a fragrance described above exhibits the effect of enhancing a preference therefor by continuous use. Moreover, the perfume composition can be formulated into a product to thereby enhance a preference for the product by repetitive use. Such a perfume composition is also incorporated in the present invention.

Perfume Composition

A perfume composition according to the present invention is characterized by comprising, as a perfume ingredient, one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Furthermore, it is more preferred that the perfume composition should comprise (I) one or more selected from the group consisting of allyl caproate, vanillin, octylaldehyde, nutmeg oil, and jasmine oil and (II) one or more selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil.

Allyl caproate, vanillin, octylaldehyde, nutmeg oil, and jasmine oil can be used alone or in combination of two or more of them as the perfume ingredient (I). In this context, allyl caproate and jasmine oil can be used particularly preferably as the perfume ingredient (I). Moreover, it is preferred that the perfume composition according to the present invention should comprise 0.1 to 50% by mass of the perfume ingredient (I) (the whole amount, when two or more perfume ingredients (I) are contained) with respect to the whole amount of the perfume composition.

Galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil can be used alone or in combination of two or more of them as the perfume ingredient (II). In this context, galaxolide and manzanate can be used particularly preferably as the perfume ingredient (II). Moreover, it is preferred that the perfume composition according to the present invention should comprise 0.1 to 30% by mass of the perfume ingredient (II) (the whole amount, when two or more perfume ingredients (II) are contained) with respect to the whole amount of the perfume composition.

The perfume composition according to the present invention may comprise, in addition to the perfume ingredients (I) and (II), other perfume ingredients in appropriate amounts. Specifically, the perfume composition according to the present invention can be used by mixing the perfume ingredients (I) and (II) and other perfume ingredients at appropriate proportions and formulating a preferable fragrance.

Even if the same perfume ingredients are used, a preference therefor and an impression of a fragrance may vary depending on perfume concentrations used. It is preferred that the perfume ingredients (I) and (II) used in the present invention should be adjusted for use to, for example, the following perfume concentrations in the perfume composition: (I) allyl caproate (0.1 to 30% by mass), vanillin (0.1 to 10% by mass), octylaldehyde (0.05 to 10% by mass), nutmeg oil (0.01 to 10% by mass), and jasmine oil (0.1 to 20% by mass); and (II) galaxolide (0.1 to 20% by mass), ambroxan (0.1 to 20% by mass), manzanate (0.1 to 20% by mass), grapefruit oil (0.1 to 50% by mass), marjoram oil (0.05 to 10% by mass), cinnamon oil (0.01 to 10% by mass), aurantiol (0.01 to 10% by mass), tomato leaf extract (0.1 to 10% by mass), spearmint oil (0.01 to 40% by mass), clove oil (0.01 to 10% by mass), chamomile oil (0.05 to 10% by mass), pepper oil (0.01 to 10% by mass), Triplal (0.01 to 10% by mass), Yuzu citron (Citrus junos) oil (0.1 to 50% by mass), bergamot oil (0.01 to 10% by mass), armoise oil (0.01 to 10% by mass), strawberry extract (0.1 to 30% by mass), geranium oil (0.1 to 20% by mass), and lime oil (0.1 to 50% by mass).

Thus, the perfume ingredients (I) and (II) can be formulated in the perfume composition to thereby obtain, in the perfume composition, the effect of giving a high preference therefor on first exposure and enhancing the preference by continuous use. Therefore, the perfume composition according to the present invention can be used directly as a preference-enhancing agent. Specifically, the perfume composition can be formulated as a preference-enhancing agent into an appropriate product to thereby enhance a preference for the product by continuous use.

The perfume composition according to the present invention may be in any form in which the perfume ingredients are vaporized and are capable of being inhaled. The perfume composition is not particularly limited by a form thereof such as a dosage form. The perfume composition according to the present invention may be used directly. Alternatively, the perfume composition according to the present invention can be formulated with solvents such as ethyl alcohol and water and can be used as fragrance cosmetics such as perfume water, eau de toilette, or eau de cologne. Moreover, these fragrance cosmetics may be blended with a variety of optional auxiliary ingredients in addition to the perfume and the solvents. Moreover, the perfume composition according to the present invention can be formulated with solvents and a variety of excipients and thereby used as a variety of fragrance agents such as room fragrances, bath fragrances, and in-car fragrances.

Moreover, the perfume composition according to the present invention can be formulated preferably into a variety of cosmetic bases or toiletry product bases. A cosmetic or toiletry product blended with the perfume composition according to the present invention can be used continuously to thereby enhance a user preference for the product. Examples of such a cosmetic or toiletry product can include creams, milky lotions, skin lotions, cosmetic powders, body lotions, soap, shampoos, rinses, treatments, body shampoos, and facial washes.

Hair Cleanser

Subsequently, a hair cleanser according to the present invention will be described.

(i) Amphoteric Surfactant

Examples of an amphoteric surfactant (i) used in the present invention include imidazoline-based amphoteric surfactants (e.g., 2-undecyl-N,N,N-(hydroxyethylcarboxymethyl)-2-imidazoline sodium and 2-cocoyl-2-imidazolinium hydroxide-1-carboxyethyloxy disodium salt) and betaine-based amphoteric surfactants (e.g., 2-alkyl-N-carboxymethyl-N-hydroxyethylimidazolinium betaine, lauryldimethylaminoacetic acid betaine, alkylbetaine, amidobetaine, and sulfobetaine).

Particularly, 2-alkyl(11-17)-N-carboxymethyl-N-hydroxyethylimidazolinium betaine and coconut oil fatty acid amidopropylbetaine can be used preferably as the amphoteric surfactant (i) of the present invention.

The amount of the amphoteric surfactant (i) formulated in the hair cleanser according to the present invention is 1 to 30% by mass, more preferably 3 to 15.0% by mass, in the whole amount of the hair cleanser. If the amount is less than 1% by mass, the resulting hair cleanser may produce poor foaming. If the amount exceeds 30% by mass, the resulting hair cleanser may have a slimy touch after use.

(ii) Cationic Polymer

Examples of a cationic polymer (ii) used in the present invention include cationized galactomannan, cationized cellulose, cationized starch, homopolymers of diallyl quaternary ammonium salts, diallyl quaternary ammonium salt/acrylamide copolymers, quaternized polyvinyl pyrrolidone derivatives, polyglycol polyamine condensates, vinylimidazolium trichloride/vinyl pyrrolidone copolymers, hydroxyethylcellulose/dimethyldiallylammonium chloride copolymers, vinyl pyrrolidone/quaternized dimethylaminoethyl methacrylate copolymers, polyvinyl pyrrolidone/alkylamino acrylate copolymers, polyvinyl pyrrolidone/alkylamino acrylate/vinyl caprolactam copolymers, vinyl pyrrolidone/methacrylamidopropyltrimethylammonium chloride copolymers, alkylacrylamide/acrylate/alkylaminoalkylacrylamide/polyethylene glycol methacrylate copolymers, and adipic acid/dimethylaminohydroxypropylethylenetriamine copolymers.

Cationized galactomannan can be used preferably as the cationic polymer (ii) of the present invention. This cation-modified galactomannan is, more specifically, a compound derived from galactomannan in which some hydroxyl groups are substituted by quaternary nitrogen-containing groups. In this context, functional groups represented by the general formula (1) below are preferable as the quaternary nitrogen-containing groups.

Formula 1

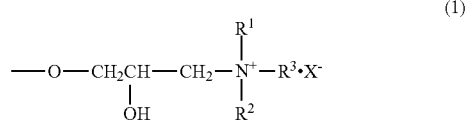

(1)

(wherein $R^1$, $R^2$, and $R^3$ each independently represent an alkyl group having 1 to 3 carbon atoms, and $X^-$ represents a monovalent anion.) $R^1$, $R^2$, and $R^3$ in the quaternary nitrogen-containing groups of the formula (1) are each independently an alkyl group having 1 to 3 carbon atoms. Among others, a methyl group is preferable. Moreover, $X^-$ is a monovalent anion. Specific examples of this anion $X^-$ include halogen atoms (such as chlorine, bromine, and iodine), methylsulfuric acid, and ethylsulfuric acid.

The quaternary nitrogen-containing group can be introduced into galactomannan according to a method conventionally known in the art. For example, a glycidyl trialkylammonium salt or 3-halogeno-2-hydroxypropyl trialkylammonium salt can be reacted with galactomannan to thereby produce the cationized galactomannan.

The content of nitrogen introduced by the cationization reaction of the cation-modified galactomannan is not particularly limited and is preferably 0.2 to 3.0% by mass. If the nitrogen content is less than 0.2% by mass, the effect of the present invention is not sufficiently observed in such a way that the resulting hair cleanser is weakly adsorbable onto hair and produces an insufficient conditioning effect. Alternatively, even if the nitrogen content exceeds 3.0% by mass, improvement in the effect is not seen.

Examples of the galactomannan constituting the cation-modified galactomannan include locust bean gum and fenugreek gum. One or more of the galactomannans are arbitrarily selected for use. For the present invention, it is preferred that the galactomannan should be locust bean gum and/or fenugreek gum.

The locust bean gum is a nonionic polysaccharide composed of a principal chain with mannose as a constitutional unit and a galactose unit as a side chain, in which the composition ratio of mannose to galactose is 4:1. The locust bean gum is natural water-soluble gum obtained from a perennial leguminous plant called *Ceratonia siliqua.*

The fenugreek gum is a nonionic polysaccharide composed of a principal chain with mannose as a constitutional unit and a galactose unit as a side chain, in which the composition ratio of mannose to galactose is 1:1. The fenugreek gum is natural water-soluble gum obtained from an annual leguminous plant.

A commercially available product may be used as the cation-modified galactomannan. Examples of the commercially available product include Catinal CLB-100 and Catinal CF-100 (both manufactured by TOHO Chemical Industry).

Moreover, the hair cleanser of the present invention may be blended with, in addition to the cationized galactomannan, other cationic polymers. Examples of the other cationic polymers include a copolymer of diallyldimethylammonium chloride and acrylamide (trade name: Merquat 550 (manufactured by NALCO Company)) or a terpolymer containing these compounds (trade name: Merquat 3331 (manufactured by NALCO Company)), and a copolymer or terpolymer containing methacrylamidopropyltrimethylammonium chloride (trade name: Merquat 2001 (manufactured by NALCO Company)).

It is preferred that the content of the cationic polymer in the hair cleanser according to the present invention should be 0.01 to 2% by mass in the whole amount of the hair cleanser. If the amount of the cationic polymer formulated therein is too small, the effect of the present invention may not sufficiently be exerted. Even if the cationic polymer is formulated in an excessive amount, enhancement in the necessary effect is not expected. The more preferable content thereof is 0.1 to 1% by mass in the whole amount of the hair cleanser.

(iii) N-acyl-N-methyltaurine-Based Anionic Surfactant

An N-acyl-N-methyltaurine-based anionic surfactant represented by the general formula (2) below can be used preferably as an N-acyl-N-methyltaurine-based anionic surfactant (hereinafter, referred to as an AMT-based surfactant) (iii) used in the present invention.

Formula 2

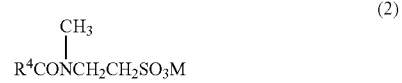

(2)

(wherein $R^4CO$ represents an aliphatic acyl group, and M represents a hydrogen atom, alkali metal, alkaline-earth metal, ammonium, organic ammonium, a basic amino acid, a taurine salt, or an N-methyltaurine salt.)

In the general formula (2), $R^4CO$ is an aliphatic acyl group and is, preferably, an aliphatic acyl group having 8 to 28 carbon atoms. If the number of carbon atoms is 7 or less, the resulting hair cleanser becomes strongly irritant to the skin and tends to have a reduced foaming property. Alternatively, if the number of carbon atoms is 29 or more, the resulting hair cleanser tends to have a reduced foaming property. The more preferable number of carbon atoms in the aliphatic acyl group is 12 to 18. An aliphatic hydrocarbon constituting the aliphatic acyl group may be saturated or unsaturated and may be linear or branched. Specific examples of the aliphatic acyl group include lauroyl groups, myristoyl groups, palmitoyl groups, stearoyl groups, oleoyl groups, coconut oil fatty acid residues, palm kernel oil fatty acid residues, and tallow fatty acid residues.

Moreover, in the general formula (2), M is a hydrogen atom, alkali metal, alkaline-earth metal, ammonium, organic ammonium, a basic amino acid, a taurine salt, or an N-methyltaurine salt. Among them, a taurine salt and a methyltaurine salt are particularly preferable. Examples of salts in the taurine salt and the N-methyltaurine salt include alkali metal, alkaline-earth metal, ammonium, and organic ammonium. Examples of the alkali metal include sodium and potassium. Examples of the alkaline-earth metal include ½ calcium and ½ magnesium. Examples of the organic ammonium include triethanolammonium. Examples of the basic amino acid include lysine and arginine.

Specific examples of the AMT-based surfactant include N-lauroyl-N-methyltaurine sodium, N-lauroyl-N-methyltaurine triethanolamine, N-lauroyl-N-methyltaurine taurine sodium, N-lauroyl-N-methyltaurine-N'-methyltaurine sodium, N-myristoyl-N-methyltaurine sodium, N-myristoyl-N-methyltaurine potassium, N— myristoyl-N-methyltaurine-N'-methyltaurine sodium, N-palmitoyl-N-methyltaurine sodium, N-stearoyl-N-methyltaurine sodium, N-oleoyl-N-methyltaurine sodium, N-coconut oil fatty acid-N-methyltaurine sodium, N-coconut oil fatty acid-N-methyltaurine potassium, N-coconut oil fatty acid-N-methyltaurine magnesium, N-coconut oil fatty acid-N-methyltaurine triethanolammonium, N-coconut oil fatty acid-N-methyltaurine taurine sodium, N-coconut oil fatty acid-N-methyltaurine-N'-methyltaurine sodium, N-palm kernel oil fatty acid-N-methyltaurine sodium, N-palm kernel oil fatty acid-N-methyltaurine lysine, N-palm kernel oil fatty acid-N-methyltaurine magnesium, N-palm kernel oil fatty acid-N-methyltaurine taurine sodium, N-palm kernel oil fatty acid-N-methyltaurine-N'-methyltaurine sodium, and N-tallow fatty acid-N-methyltaurine sodium. In this context, when the acyl group is acyl in fatty acid derived from fat or oil and this acyl is represented by the name of the fat or oil fatty acid, the acyl is simply represented by the indication of the fat or oil fatty acid. For example, the "N-coconut oil fatty acid" of an N-coconut oil fatty acid-N-methyltaurine salt represents an acyl group derived from the coconut oil fatty acid at the N position. Specifically, it means "N-cocoyl". The same holds true for the descriptions below of the present invention.

Among the specific examples of the AMT-based surfactant, N-lauroyl-N-methyltaurine sodium, N-lauroyl-N-methyltaurine taurine sodium, N-lauroyl-N-methyltaurine-N'-methyltaurine sodium, N-coconut oil fatty acid-N-methyltaurine sodium, N-coconut oil fatty acid-N-methyltaurine taurine sodium, and N-coconut oil fatty acid-N-methyltaurine-N'-methyltaurine sodium are preferable. One or more of the AMT-based surfactants are arbitrarily selected and formulated.

It is preferred that the content of the AMT-based surfactant in the hair cleanser according to the present invention should be 0.1 to 30% by mass in the whole amount of the hair cleanser. If the amount of the AMT-based surfactant formulated therein is too small, the effect of the present invention may not sufficiently be exerted. Even if the AMT-based surfactant is formulated in an excessive amount, enhancement in the necessary effect is not expected. The more preferable content of the AMT-based surfactant is 1 to 20% by mass.

In the present invention, the hair cleanser can be blended with other surfactants usually used without impairing the effect of the present invention.

Specific examples of anionic surfactants include alkyl sulfate, alkyl ether sulfate, higher fatty acid salts, alkyl sulfonate, polyoxyethylene alkyl sulfate, alkyl benzene sulfonate, N-acylsarcosine salts, N-acyl isethionate, N-acyl glutamate, alpha-olefin sulfonate, alkyl ether acetate, and polyoxyethylene alkyl ether acetate.

Specific examples of nonionic surfactants include alkanolamide, glycerin fatty acid ester, polyoxyalkylene alkyl ether, polyoxyalkylene glycol, polyoxyalkylene sorbitan fatty acid ester, sorbitan fatty acid ester, polyoxyalkylene sorbitol fatty acid ester, sorbitol fatty acid ester, polyoxyalkylene glycerin fatty acid ester, polyoxyalkylene fatty acid ester, polyoxyalkylene alkylphenyl ether, tetrapolyoxyalkylene ethylenediamine condensates, polyoxyalkylene ether, sucrose fatty acid ester, polyoxyalkylene fatty acid amide, polyoxyalkylene glycol fatty acid ester, polyoxyalkylene castor oil derivatives, polyoxyalkylene hydrogenated castor oil derivatives, and alkylpolyglucoside.

(iv) Ingredient

An ingredient (iv) used in the present invention is one or more ingredients selected from the group consisting of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

In the hair cleanser of the present invention, any one of the ingredients (iv) can be used alone. Alternatively, two or more of them can be used in combination. In this context, allyl caproate, vanillin, octylaldehyde, nutmeg oil, or jasmine oil can be used particularly preferably as the (iv) ingredient.

It is preferred that the content of the ingredient (iv) (the whole amount, when two or more ingredients (iv) are contained) in the hair cleanser according to the present invention should be 0.001 to 0.6% by mass in the whole amount of the hair cleanser. If the amount of the ingredient (iv) formulated therein is too small, the effect of the present invention may not sufficiently be exerted. Even if the ingredient (iv) is formulated in an excessive amount, the necessary effect may not be expected. In the present invention, the ingredient (iv) can be formulated to thereby improve the usability of the cleanser. Thus, the present invention may be applied as a usability-improving agent and a method for improving usability.

Moreover, the hair cleanser of the present invention may be blended with a reactive silicone-based block copolymer represented by the general formula (3) below in addition to the essential ingredients (i) to (iv).

Formula 3

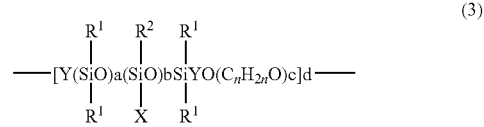

In the formula (3), $R^1$ is each independently a monovalent hydrocarbon group free from aliphatic unsaturation. Examples thereof include methyl groups, ethyl groups, propyl groups, butyl groups, octyl groups, dodecyl groups, phenyl groups, and phenethyl groups. Methyl groups, ethyl groups, and phenyl groups are preferable. Particularly, methyl groups are preferable.

$R^3$ in the X group is a direct bond or a divalent hydrocarbon group having 1 to 20 carbon atoms. Examples of such a divalent hydrocarbon group include —$CH_2$—, —$CH_2CH_2$—, —$CH_2CH_2CH_2$—, —$CH(CH_3)CH_2$—, —$(CH_2)_4$—, —$(CH_2)_6$—, —$(CH_2)_8$—, —$CH_2CH_2C_6H_4$—, —$(CH_2)_{12}$—, and —$(CH_2)_{16}$—. Preferably, $R^3$ is a propylene group.

Moreover, Z in the X group represents an amino group-containing group, ammonium group-containing group, or epoxy group-containing group. Specific examples of the X group include, but not limited to:

Formula 4

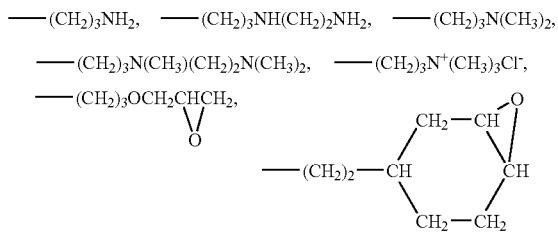

It is preferred in terms of the effect the X group should be an amino group-containing group such as —$(CH_2)_3NH_2$, —$(CH_2)_3NH(CH_2)_2NH_2$, —$(CH_2)_3N(CH_3)_2$, or —$(CH_2)_3N(CH_3)(CH_2)_2N(CH_3)_2$ or an ammonium group-containing group such as —$(CH_2)_3N^+(CH_3)_3Cl^-$.

In the formula (3), Y is a divalent organic group. One of the bond ends thereof is bonded to an adjacent silicon atom through carbon-silicon. The other bond end is bonded to a polyoxyalkylene block through the oxygen atom.

Examples of the divalent organic group represented by Y include —$R^4$—, —$R^4$—CO—, —$R^4$—NHCO—, —$R^4$—NHCONHR$^5$—NHCO—, and —$R^4$—OOCNH—$R^5$—NHCO— (wherein $R^4$ is a divalent alkylene group, for example, an ethylene group, propylene group, or butylene group, and $R^5$ is a divalent alkyl group, for example, any of the groups illustrated as $R^4$ or a divalent allylene group, for example, —$C_6H_4$—, —$C_6H_4$—$C_6H_4$—, —$C_6H_4$—$CH_2$—$C_6H_4$—, or —$C_6H_4$—CH($CH_3$)—$C_6H_4$—). The Y group is, preferably, —$CH_2CH_2$—, —$CH_2CH_2CH_2$—, —$CH_2CH(CH_3)CH_2$—, —$CH_2CH_2CH_2CH_2$—, —$(CH_2)_2CO$—, —$(CH_2)_3NHCO$—, —$(CH_2)_3NHCONHC_6H_4NHCO$—, or —$(CH_2)_3OOCNHC_6H_4NHCO$—. A particularly preferable Y group is a divalent alkylene group (—$CH_2CH_2$—, —$CH_2CH_2CH_2$—, —$CH_2CH(CH_3)CH_2$—, etc.). —$CH_2CH(CH_3)CH_2$— is most preferable.

In the formula (3), n is an integer of 2 to 4, preferably 2 to 3, more preferably 2. The polyoxyalkylene block may be composed of only one kind of oxyalkylene group or may contain two or more kinds of oxyalkylene groups.

The reactive silicone-based block copolymer can be produced by use of a method known in the art. For example, a method described in Japanese Patent Publication No. 5-310944 can be used. Moreover, SILSTYLE series (Dow Corning Toray) can be used. Furthermore, a (bis-isobutyl PEG-14/amodimethicone) copolymer can be used preferably.

In the present invention, one or more of the reactive silicone-based block copolymers can be used.

The amount of the reactive silicone-based block copolymer formulated therein is not particularly limited and is preferably 0.01 to 10% by mass, more preferably 0.01 to 5% by mass, particularly preferably 0.01 to 2% by mass, in the whole amount of the hair cleanser. If the amount is too small, the effect is not sufficiently exerted. Even if the amount is too large, proper enhancement in the effect is not expected. Rather, the reactive silicone-based block copolymer formulated in too a large amount may adversely affect the texture of the hair cleanser.

The hair cleanser of the present invention can be blended with a silicone emulsion in addition to the essential ingredients. The silicone emulsion according to the present invention is an emulsion in which droplets particles of water-insoluble silicone oil are present as dispersed droplets in water.

The silicone emulsion formulated therein can impart a light touch to the hair cleanser without impairing rich velvet-like texture. Moreover, the resulting hair cleanser can rinse out much more quickly.

The silicone oil in the silicone emulsion is not particularly limited. Specific examples thereof include methylpolysiloxane, methylphenylpolysiloxane, and decamethylcyclopentasiloxane. In the present invention, non-volatile silicone oil is preferable. Methylpolysiloxane is particularly preferable. One or more of the silicone emulsions can be selected arbitrarily and formulated.

Silicone emulsions are commercially available. Therefore, a commercially available product can be used as the silicon emulsion of the present invention and is efficient. Examples of the commercially available product include dimethyl silicone emulsions BY22-007 (which contains 50% by mass of dimethylpolysiloxane), BY22-009 (which contains 20% by mass of ultrafine-powdered methylpolysiloxane), BY22-029 (which contains 50% by mass of highly polymerized methylpolysiloxane), BY22-019 (which contains 50% by mass of highly polymerized methylpolysiloxane and decamethylcyclopentasiloxane), BY22-034 (which contains 50% by mass of highly polymerized methylpolysiloxane and methylpolysiloxane), and BY22-020 (which contains 50% by mass of highly polymerized methylpolysiloxane and light liquid isoparaffin) (all manufactured by Dow Corning Toray Co., Ltd.).

The amount of the silicone emulsion formulated therein is not particularly limited and is preferably 0.0005 to 5% by mass in terms of a silicone oil amount in the whole amount of the cleanser composition. More preferably, the amount is 0.25 to 2.5% by mass in the whole amount of the cleanser composition.

The hair cleanser of the present invention can be blended appropriately with, in addition to the ingredients, other optional ingredients usually used in hair cleansers, as required, without impairing the effect of the present invention. Examples of the other ingredients that may be formulated therein include oil, pearly luster-imparting agents, moisturizing agents, polyhydric alcohol, polymer-based viscosity modifiers, amino acids (glutamic acid, arginine, etc.), perfumes, pigments, UV absorbers, antioxidants, germicides, anti-inflammatory agents, antiseptics, sequestering agents, and water.

Specific examples of the oil include squalane, olive oil, jojoba oil, castor oil, lanoline, liquid paraffin, cetanol, and stearyl alcohol. Examples of the pearly luster-imparting agents include ethylene glycol distearate and styrene polymers.

Specific examples of the moisturizing agents include polyethylene glycol, glycerin, 1,3-butanediol, 1,2-pentanediol, erythritol, sorbitol, xylitol, maltitol, propylene glycol, dipropylene glycol, diglycerin, sodium pyrrolidone carboxylate, lactic acid, and sodium lactate.

Specific examples of the polymer-based viscosity modifiers include methylcellulose, hydroxyethylcellulose, and carboxymethylcellulose.

The hair cleanser of the present invention can be produced by a standard method and prepared into dosage forms such as paste, gel, liquid, solid, and mousse forms.

Example 1

Hereinafter, the present invention will be described more specifically with reference to Examples. However, the present invention is not limited to them.

Relationship Between Continuous Use of Fragrance and Preference Therefor

First of all, the present inventors studied the relationship between the continuous use of a fragrance and a preference therefor and therefore conducted by use of six prepared perfumes whose fragrances were formulated in advance, an evaluation of a preference under each of the condition in which panelists did not take a smell at the prepared perfumes beforehand (on first exposure) and the condition in which panelists took a smell at the prepared perfumes twice in advance (after two exposures). Details of the test and evaluation criteria are shown below. An average value of evaluation results of preferences for a fragrance by the panelists who took a smell twice in advance (after two exposures) and an average value of evaluation results of preferences for the fragrance by the panelists who did not take a smell beforehand (on first exposure) were calculated for each of the perfumes. The results are shown in Table 1 below and FIG. 1.

Details of Test

Six prepared perfumes were prepared. Panelists took a smell at three of them twice in advance at a 5-minute interval. After another 5-minute interval, an evaluation was conducted of preferences for all of the six perfumes including these three perfumes at which the panelists took a smell twice in advance and the remaining three perfumes at which the panelists did not take a smell. The number of the panelists was 22 in total. The fragrances at which the panelists took a smell twice in advance and the fragrances at which the panelists did not take a smell were assigned to each panelist under counterbalance conditions.

Evaluation Criteria

"Preference": A total of 22 panelists took a smell at the fragrances of three target perfumes and rated "preferences" for the target perfumes on a scale of 1 to 7 according to evaluation criteria below.

| <Evaluation criteria> | |
|---|---|
| Very like | 7 |
| Like | 6 |
| Moderately like | 5 |
| Neither like nor dislike | 4 |
| Moderately dislike | 3 |
| Dislike | 2 |
| Very dislike | 1 |

TABLE 1

| Prepared perfume | Preference (on first exposure) | Preference (after two exposures) |
|---|---|---|
| 1 | 5.0 | 4.0 |
| 2 | 4.0 | 4.3 |
| 3 | 4.3 | 4.7 |

TABLE 1-continued

| Prepared perfume | Preference (on first exposure) | Preference (after two exposures) |
|---|---|---|
| 4 | 4.3 | 5.0 |
| 5 | 3.3 | 6.3 |
| 6 | 3.7 | 6.7 |

Table 1 above and FIG. 1 demonstrated that for five of the six prepared perfumes, the impressions of preferences are evaluated as being increased after two exposures as compared with on first exposure. Moreover, change in preference was observed to differ depending on the kinds of the prepared perfumes. Therefore, it was shown that fragrances are classified into those easily enhancing a preference therefor by preliminary exposure and those not easily enhancing a preference therefor by preliminary exposure.

Change in Preferences for Various Perfume Ingredients by Continuous Use

Subsequently, the present inventors studied change in preferences for various perfume ingredients by continuous use and therefore conducted an evaluation of preferences for 48 perfume ingredients known in the art on first exposure and after two exposures in the same way as in the test above. The results are shown in Tables 2 and 3. Moreover, the change in preferences between on first exposure and after two exposures is summarized in FIG. 2.

TABLE 2

| Perfume ingredient | Preference (on first exposure) | Preference (after two exposures) |
|---|---|---|
| Litchi extract (5%) | 3.1 | 2.0 |
| Raspberry ketone (1%) | 4.2 | 3.1 |
| Cedarwood oil (5%) | 2.6 | 1.7 |
| Calone (0.05%) | 4.8 | 4.0 |
| Ylang-ylang oil (0.5%) | 3.8 | 3.1 |
| Lavender oil (1%) | 3.8 | 3.1 |
| Ginger oil (0.5%) | 4.3 | 3.5 |
| Coumarin (0.5%) | 3.2 | 2.5 |
| Lilial (0.05%) | 3.6 | 3.0 |
| β-damascone (1%) | 4.8 | 4.3 |
| β-ionone (0.1%) | 4.8 | 4.3 |
| Anethole (0.5%) | 2.6 | 2.1 |
| Cumin oil (0.1%) | 3.3 | 2.8 |
| Rose oil (0.5%) | 5.0 | 4.5 |
| γ-undecalactone (0.01%) | 4.8 | 4.5 |
| Prune extract (0.5%) | 4.6 | 4.3 |
| Cassis extract (10%) | 4.1 | 3.9 |
| cis-jasmone (0.5%) | 2.8 | 2.6 |
| Heliotropin (1%) | 3.9 | 3.8 |
| Peppermint oil (3%) | 4.8 | 4.6 |
| Sandalwood oil (5%) | 3.1 | 2.9 |
| Isoananate (0.01%) | 4.0 | 3.9 |
| Patchouli oil (5%) | 1.7 | 1.7 |
| Undecylenic aldehyde (0.05%) | 2.5 | 2.5 |

TABLE 3

| Perfume ingredient | Preference (on first exposure) | Preference (after two exposures) |
|---|---|---|
| Galaxolide (10%) | 3.5 | 3.6 |
| Ambroxan (1%) | 3.2 | 3.4 |
| Manzanate (1%) | 4.7 | 5.0 |
| Grapefruit oil (10%) | 5.8 | 6.2 |
| Marjoram oil (5%) | 2.6 | 3.1 |
| Cinnamon oil (0.5%) | 2.7 | 3.2 |
| Aurantiol (10%) | 2.8 | 3.3 |
| Tomato leaf extract (0.5%) | 3.9 | 4.4 |

TABLE 3-continued

| Perfume ingredient | Preference (on first exposure) | Preference (after two exposures) |
|---|---|---|
| Spearmint oil (3%) | 4.3 | 4.9 |
| Clove oil (1%) | 2.6 | 3.2 |
| Chamomile oil (1%) | 2.3 | 2.9 |
| Pepper oil (0.5%) | 2.8 | 3.5 |
| Triplal (0.1%) | 2.9 | 3.6 |
| Yuzu citron oil (10%) | 4.3 | 5.0 |
| Octylaldehyde (0.1%) | 4.4 | 5.1 |
| Vanillin (5%) | 3.1 | 3.8 |
| Jasmine oil (1%) | 1.9 | 2.7 |
| Bergamot oil (10%) | 3.7 | 4.6 |
| Armoise oil (0.5%) | 2.5 | 3.5 |
| Strawberry extract (10%) | 3.8 | 4.8 |
| *Geranium* oil (5%) | 2.6 | 3.8 |
| Lime oil (10%) | 3.0 | 4.2 |
| Nutmeg oil (0.5%) | 2.6 | 3.9 |
| Allyl caproate (10%) | 2.7 | 4.1 |

Figure 2:
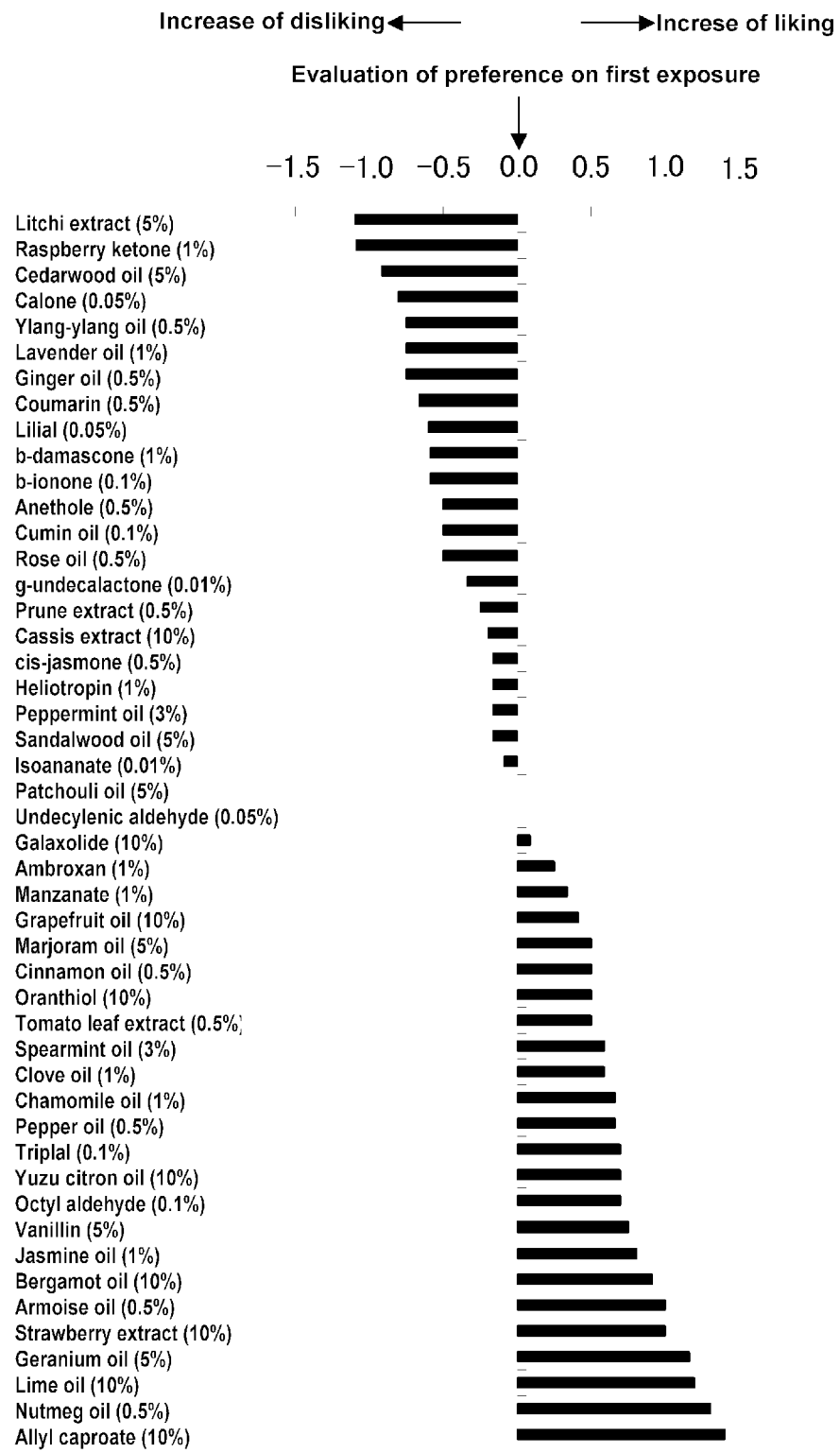
FIG. 2 is a diagram summarizing change in evaluation results of preferences between on first exposure and after two exposures by conducing an evaluation of preferences for 48 perfume ingredients known in the art on first exposure and after two exposures.

Tables 2 and 3 above and FIG. 2 demonstrated that for 24 of the 48 perfume ingredients known in the art, the impressions of preferences are evaluated as being increased after two exposures as compared with on first exposure. Moreover, the degree of change in preferences attributed to the number of exposures differed depending on the kinds of the perfume ingredients. Thus, it was shown that various perfume ingredients are classified into those easily enhancing a preference therefor by continuous use and those not easily enhancing a preference therefor by continuous use. Most of these 24 perfume ingredients totally differed in fragrance note classification (e.g., allyl caproate has a fruity note, whereas nutmeg oil has a spicy note). Thus, it was also shown that the perfume ingredient that enhances a preference therefor by continuous use is not simply determined by the relationship with the kind of a fragrance note.

Study of Combination of Perfume Ingredients

It was thus demonstrated that for the 24 perfume ingredients shown in Table 3 above, the impressions of preferences are evaluated as being increased after two exposures as compared with on first exposure. However, the impressions of preferences on the first exposure tend to be evaluated as being low as a whole. For example, allyl caproate, which was evaluated as having the highest effect of enhancing a preference therefor by continuous use, was rated as low as 2.7 in terms of the preference on first exposure. Therefore, this perfume ingredient may present a problem when used alone in actual use.

Figure 3:
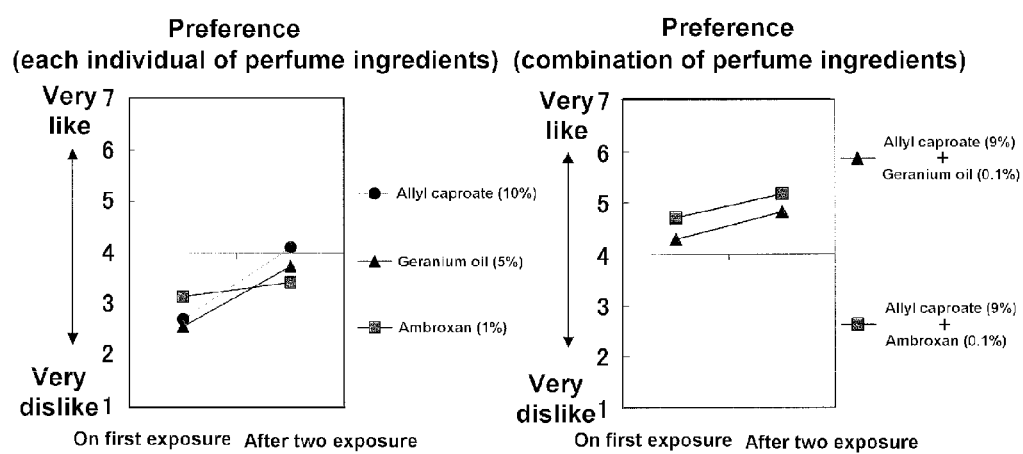
FIG. 3 shows evaluation results of preferences for perfume compositions comprising allyl caproate in combination with geranium oil or ambroxan (and each individual of the perfume ingredients) on first exposure and after two exposures.

Thus, the present inventors studied, on allyl caproate, combination with other perfume ingredients that enhance a preference for the combined fragrance on first exposure. An evaluation of preferences for each perfume composition on first exposure and after two exposures was conducted in the same way as the test above on a perfume composition comprising allyl caproate in combination with geranium oil or ambroxan. The results are shown in Table 4 below and FIG. 3 together with evaluation results of each individual of the perfume ingredients.

TABLE 4

| Perfume ingredient | Preference (on first exposure) | Preference (after two exposures) |
|---|---|---|
| Allyl caproate (10%) | 2.7 | 4.1 |
| *Geranium* oil (5%) | 2.6 | 3.8 |
| Ambroxan (1%) | 3.2 | 3.4 |
| Allyl caproate (9%) + geranium oil (0.1%) | 4.3 | 4.9 |
| Allyl caproate (9%) + ambroxan (0.1%) | 4.7 | 5.2 |

Moreover the present inventors conducted further detailed study. As a result, it was demonstrated that a perfume ingredient that gives a low preference therefor by itself on first exposure, such as allyl caproate, vanillin, octylaldehyde, nutmeg oil, or jasmine oil, can be used in combination with any perfume ingredient of galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, bergamot oil, armoise oil, strawberry extract, geranium oil, and lime oil to thereby significantly enhance the preference on first exposure and to thereby obtain a perfume composition that enhances a preference therefor by continuous use.

Correlation Between Change in Preference by Continuous Use and Evaluation of Impression of Fragrance Subsequently, the present inventors studied the correlation between change in preference by continuous use and evaluation of an impression of a fragrance and therefore evaluated the perfume ingredients used in the test above for each impression such as "clarity", "cheerfulness", "density", "intensity", "stuffy", "mellowness", "sweetness", and "refreshing". Furthermore, the present inventors determined, from the obtained evaluation results of an impression of a fragrance, the correlation coefficient between each evaluation item of an impression of a fragrance and a value of change in preference by continuous use. Evaluation criteria are shown below. In this context, the impression of a fragrance was evaluated under two conditions of on first exposure and after two exposures, as in the test above. The results are shown in Tables 5 and 6 below.

Evaluation Criteria

"Clarity": 192 panelists took a smell at the target perfume and two comparative perfumes and rated an impression of the "clarity" of the target perfume on a scale of 1 to 7 according to evaluation criteria below by comparing it with that of the comparative perfumes. In this context, Cedarwood oil and peppermint oil were used as the comparative perfumes to conduct the evaluation with respect to a "clarity" evaluation of Cedarwood oil rated 3.0 and a "clarity" evaluation of peppermint oil rated 5.0. In this context, an average value obtained by dividing, by the number of the panelists, the total sum of the scores given by the panelists is used as an evaluation value of the impression of "clarity".

| <Evaluation criteria> | |
|---|---|
| Very perceivable | 7 |
| Perceivable | 6 |
| Moderately perceivable | 5 |
| Neither perceivable nor unperceivable | 4 |
| Less perceivable | 3 |
| Unperceivable | 2 |
| Completely unperceivable | 1 |

"Cheerfulness": 192 panelists took a smell at the target perfume and two comparative perfumes and rated an impression of the "cheerfulness" of the target perfume on a scale of 1 to 7 according to the evaluation criteria above by comparing it with that of the comparative perfumes. In this context, patchouli oil and grapefruit oil were used as the comparative perfumes to conduct the evaluation with respect to a "cheerfulness" evaluation of patchouli oil rated 2.0 and a "cheerfulness" evaluation of grapefruit oil rated 6.0. In this context, an average value obtained by dividing, by the number of the panelists, the total sum of the scores given by the panelists is used as an evaluation value of the impression of "cheerfulness".

"Density": 192 panelists took a smell at the target perfume and two comparative perfumes and rated an impression of the "density" of the target perfume on a scale of 1 to 7 according to the evaluation criteria above by comparing it with that of the comparative perfumes. In this context, calone and geranium oil were used as the comparative perfumes to conduct the evaluation with respect to a "density" evaluation of calone rated 3.0 and a "density" evaluation of geranium oil rated 5.5. In this context, an average value obtained by dividing, by the number of the panelists, the total sum of the scores given by the panelists is used as an evaluation value of the impression of "density".

"Intensity": 192 panelists took a smell at the target perfume and two comparative perfumes and rated an impression of the "intensity" of the target perfume on a scale of 1 to 7 according to the evaluation criteria above by comparing it with that of the comparative perfumes. In this context, β-damascone and allyl caproate were used as the comparative perfumes to conduct the evaluation with respect to an "intensity" evaluation of β-damascone rated 3.5 and an "intensity" evaluation of allyl caproate rated 6.0. In this context, an average value obtained by dividing, by the number of the panelists, the total sum of the scores given by the panelists is used as an evaluation value of the impression of "intensity".

"Stuffy": 192 panelists took a smell at the target perfume and two comparative perfumes and rated an impression of the "stuffy" of the target perfume on a scale of 1 to 7 according to the evaluation criteria above by comparing it with that of the comparative perfumes. In this context, heliotropin and tomato leaf extract were used as the comparative perfumes to conduct the evaluation with respect to a "stuffy" evaluation of heliotropin rated 3.0 and a "stuffy" evaluation of tomato leaf extract rated 4.0. In this context, an average value obtained by dividing, by the number of the panelists, the total sum of the scores given by the panelists is used as an evaluation value of the impression of "stuffy".

"Mellowness": 192 panelists took a smell at the target perfume and two comparative perfumes and rated an impression of the "mellowness" of the target perfume on a scale of 1 to 7 according to the evaluation criteria above by comparing it with that of the comparative perfumes. In this context, spearmint oil and rose oil were used as the comparative perfumes to conduct the evaluation with respect to a "mellowness" evaluation of spearmint oil rated 3.0 and a "mellowness" evaluation of rose oil rated 4.5. In this context, an average value obtained by dividing, by the number of the panelists, the total sum of the scores given by the panelists is used as an evaluation value of the impression of "mellowness".

"Sweetness": 192 panelists took a smell at the target perfume and two comparative perfumes and rated an impression of the "sweetness" of the target perfume on a scale of 1 to 7 according to the evaluation criteria above by comparing it with that of the comparative perfumes. In this context, cis-jasmone and ylang-ylang oil were used as the comparative perfumes to conduct the evaluation with respect to a "sweetness" evaluation of cis-jasmone rated 2.5 and a "sweetness" evaluation of ylang-ylang oil rated 4.5. In this context, an average value obtained by dividing, by the number of the panelists, the total sum of the scores given by the panelists is used as an evaluation value of the impression of "sweetness".

"Refreshing": 192 panelists took a smell at the target perfume and two comparative perfumes and rated an impression of the "refreshing" of the target perfume on a scale of 1 to 7 according to the evaluation criteria above by comparing it with that of the comparative perfumes. In this context, allyl caproate and spearmint oil were used as the comparative perfumes to conduct the evaluation with respect to a "refreshing" evaluation of allyl caproate rated 1.9 and a "refreshing" evaluation of spearmint oil rated 5.8. In this context, an average value obtained by dividing, by the number of the panelists, the total sum of the scores given by the panelists is used as an evaluation value of the impression of "refreshing".

TABLE 5

| Impression of fragrance | Correlation coefficient amount of change in preference vs. impression evaluation of fragrance on first exposure |
|---|---|
| Clarity | −0.193 |
| Cheerfulness | −0.116 |
| Density | 0.480 |
| Intensity | 0.480 |
| Stuffy | 0.422 |
| Mellowness | −0.286 |
| Sweetness | 0.042 |
| Refreshing | 0.127 |

TABLE 6

| Impression of fragrance | Correlation coefficient preference evaluation vs. impression evaluation of fragrance on first exposure | Correlation coefficient preference evaluation vs. impression evaluation of fragrance after two exposures |
|---|---|---|
| Clarity | 0.735 | 0.682 |
| Cheerfulness | 0.875 | 0.897 |
| Density | −0.399 | −0.224 |
| Intensity | −0.444 | −0.314 |
| Stuffy | −0.578 | −0.549 |
| Mellowness | 0.713 | 0.710 |
| Sweetness | 0.493 | 0.573 |
| Refreshing | 0.280 | 0.397 |

Table 5 above shows the correlation coefficient between an evaluation of impressions of a fragrance on first exposure and an amount of change in preference from on first exposure to after two exposures. As seen in this table, the "density" or "intensity" of a fragrance on first exposure correlates with the amount of change in preference. This shows that a fragrance as being high evaluation of "density" or "intensity" on first exposure exhibits a large increase in preference after two exposures, whereas a fragrance as being low evaluation of "density" or "intensity" on first exposure exhibits a reduction in preference after two exposures. Table 6 above shows the correlation between an evaluation of preferences for a fragrance on first exposure and after two exposures and an evaluation of an impression of the fragrance. As can be seen in this table, the correlation between the preference and "cheerfulness" is highest both on first exposure and after two exposures, showing that a fragrance that gives a high preference therefor is also evaluated as being high in the impression of "cheerfulness". This shows that a fragrance for which a preference is evaluated as being increased after two exposures as compared with on first exposure also exhibits an increase in "cheerfulness". From these results, it is deduced that change in preference for a perfume ingredient by continuous use is strongly linked to evaluations of impressions of the "density" and the "cheerfulness" of the perfume ingredient and to changes in the impressions.

Relationship Between Perfume Ingredient that Enhances Preference Therefor by Continuous Use and Evaluations of Impressions of "Density" and "Cheerfulness" Thereof.

From these test results, the present inventors deduced that enhancement in preference by continuous use is strongly linked to evaluations of impressions of the "density" and the "cheerfulness" thereof and to changes in the impressions. In this regard, the present inventors conducted further detailed study by comparing change in preferences for various perfume ingredients by continuous use with evaluation results of impressions of "density" and "cheerfulness". The respective evaluation results are summarized and shown in Tables 7 and 8 below and FIG. 4.

increased by continuous use. In a perfume ingredient that reduces a preference therefor by continuous use, by contrast, it was confirmed that an impression of the "density" thereof is evaluated as being increased by continuous use, and an impression of the "cheerfulness" thereof is evaluated as being reduced by continuous use. From these results, it was shown that the impression of the "density" of a perfume ingredient needs to be evaluated as being reduced by continuous use or the impression of the "cheerfulness" of a perfume ingredient

TABLE 7

| Perfume ingredient | Preference (first) | Preference (twice) | "Density" (first) | "Density" (twice) | "Cheerfulness" (first) | "Cheerfulness" (twice) |
|---|---|---|---|---|---|---|
| *Litchi* extract (5%) | 3.1 | 2.0 | 4.2 | 4.1 | 3.2 | 3.0 |
| Raspberry ketone (1%) | 4.2 | 3.1 | 3.3 | 3.8 | 4.5 | 3.3 |
| Cedarwood oil (5%) | 2.6 | 1.7 | 4.6 | 4.8 | 2.8 | 2.4 |
| Calone (0.05%) | 4.8 | 4.0 | 3.0 | 2.9 | 5.1 | 4.0 |
| Ylang-ylang oil (0.5%) | 3.8 | 3.1 | 4.7 | 5.0 | 3.9 | 4.3 |
| Lavender oil (1%) | 3.8 | 3.1 | 4.6 | 5.3 | 4.6 | 3.7 |
| Ginger oil (0.5%) | 4.3 | 3.5 | 3.7 | 4.0 | 4.3 | 4.0 |
| Coumarin (0.5%) | 3.2 | 2.5 | 3.7 | 5.3 | 3.1 | 3.1 |
| Lilial (0.05%) | 3.6 | 3.0 | 3.2 | 2.2 | 3.4 | 3.5 |
| β-damascone (1%) | 4.8 | 4.3 | 3.2 | 2.4 | 4.3 | 4.4 |
| β-ionone (0.1%) | 4.8 | 4.3 | 3.3 | 3.2 | 4.7 | 4.1 |
| Anethole (0.5%) | 2.6 | 2.1 | 4.6 | 4.2 | 3.4 | 2.6 |
| Cumin oil (0.1%) | 3.3 | 2.8 | 3.0 | 3.8 | 3.8 | 3.4 |
| Rose oil (0.5%) | 5.0 | 4.5 | 3.8 | 4.8 | 5.3 | 5.1 |
| γ-undecalactone (0.01%) | 4.8 | 4.5 | 2.7 | 3.6 | 4.3 | 4.4 |
| Prune extract (0.5%) | 4.6 | 4.3 | 3.0 | 4.0 | 4.4 | 4.2 |
| *Cassis* extract (10%) | 4.1 | 3.9 | 3.5 | 3.8 | 4.8 | 4.4 |
| cis-jasmone (0.5%) | 2.8 | 2.6 | 2.9 | 3.6 | 3.1 | 3.2 |
| Heliotropin (1%) | 3.9 | 3.8 | 2.7 | 2.8 | 3.3 | 3.8 |
| Peppermint oil (3%) | 4.8 | 4.6 | 3.7 | 4.3 | 5.1 | 4.9 |
| Sandalwood oil (5%) | 3.1 | 2.9 | 4.1 | 4.8 | 3.0 | 3.0 |
| Isoananate (0.01%) | 4.0 | 3.9 | 2.9 | 3.3 | 4.1 | 3.7 |
| Patchouli oil (5%) | 1.7 | 1.7 | 5.7 | 4.8 | 2.0 | 3.3 |
| Undecylenic aldehyde (0.05%) | 2.5 | 2.5 | 2.4 | 2.6 | 2.4 | 2.3 |

TABLE 8

| Perfume ingredient | Preference (first) | Preference (twice) | "Density" (first) | "Density" (twice) | "Cheerfulness" (first) | "Cheerfulness" (twice) |
|---|---|---|---|---|---|---|
| Galaxolide (10%) | 3.5 | 3.6 | 3.4 | 4.0 | 3.8 | 3.3 |
| Ambroxan (1%) | 3.2 | 3.4 | 4.3 | 2.8 | 3.6 | 3.1 |
| Manzanate (1%) | 4.7 | 5.0 | 3.9 | 3.8 | 4.6 | 4.8 |
| Grapefruit oil (10%) | 5.8 | 6.2 | 5.1 | 3.5 | 6.0 | 5.9 |
| Marjoram oil (5%) | 2.6 | 3.1 | 4.4 | 5.0 | 2.8 | 3.1 |
| Cinnamon oil (0.5%) | 2.7 | 3.2 | 5.2 | 5.3 | 4.0 | 3.3 |
| Aurantiol (10%) | 2.8 | 3.3 | 4.6 | 5.3 | 3.6 | 4.1 |
| Tomato leaf extract (0.5%) | 3.9 | 4.4 | 4.1 | 4.0 | 4.2 | 4.7 |
| Spearmint oil (3%) | 4.3 | 4.9 | 4.3 | 4.4 | 4.3 | 5.3 |
| Clove oil (1%) | 2.6 | 3.2 | 4.2 | 5.0 | 3.0 | 3.1 |
| Chamomile oil (1%) | 2.3 | 2.9 | 4.8 | 4.4 | 2.7 | 3.1 |
| Pepper oil (0.5%) | 2.8 | 3.5 | 4.1 | 3.3 | 3.2 | 3.5 |
| Triplal (0.1%) | 2.9 | 3.6 | 2.2 | 3.5 | 3.0 | 4.1 |
| Yuzu citron oil (10%) | 4.3 | 5.0 | 3.6 | 3.7 | 4.5 | 5.6 |
| Octylaldehyde (0.1%) | 4.4 | 5.1 | 4.0 | 2.5 | 4.7 | 5.9 |
| Vanillin (5%) | 3.1 | 3.8 | 5.9 | 5.5 | 3.3 | 3.8 |
| Jasmine oil (1%) | 1.9 | 2.7 | 5.6 | 4.1 | 3.3 | 3.3 |
| Bergamot oil (10%) | 3.7 | 4.6 | 5.4 | 4.8 | 4.6 | 4.7 |
| Armoise oil (0.5%) | 2.5 | 3.5 | 5.1 | 4.3 | 3.7 | 3.9 |
| Strawberry extract (10%) | 3.8 | 4.8 | 5.4 | 4.4 | 5.0 | 5.5 |
| *Geranium* oil (5%) | 2.6 | 3.8 | 5.5 | 5.2 | 3.3 | 3.8 |
| Lime oil (10%) | 3.0 | 4.2 | 4.6 | 4.5 | 3.8 | 5.0 |
| Nutmeg oil (0.5%) | 2.6 | 3.9 | 4.3 | 4.3 | 3.5 | 4.6 |
| Allyl caproate (10%) | 2.7 | 4.1 | 4.9 | 4.7 | 3.4 | 4.2 |

Figure 4:
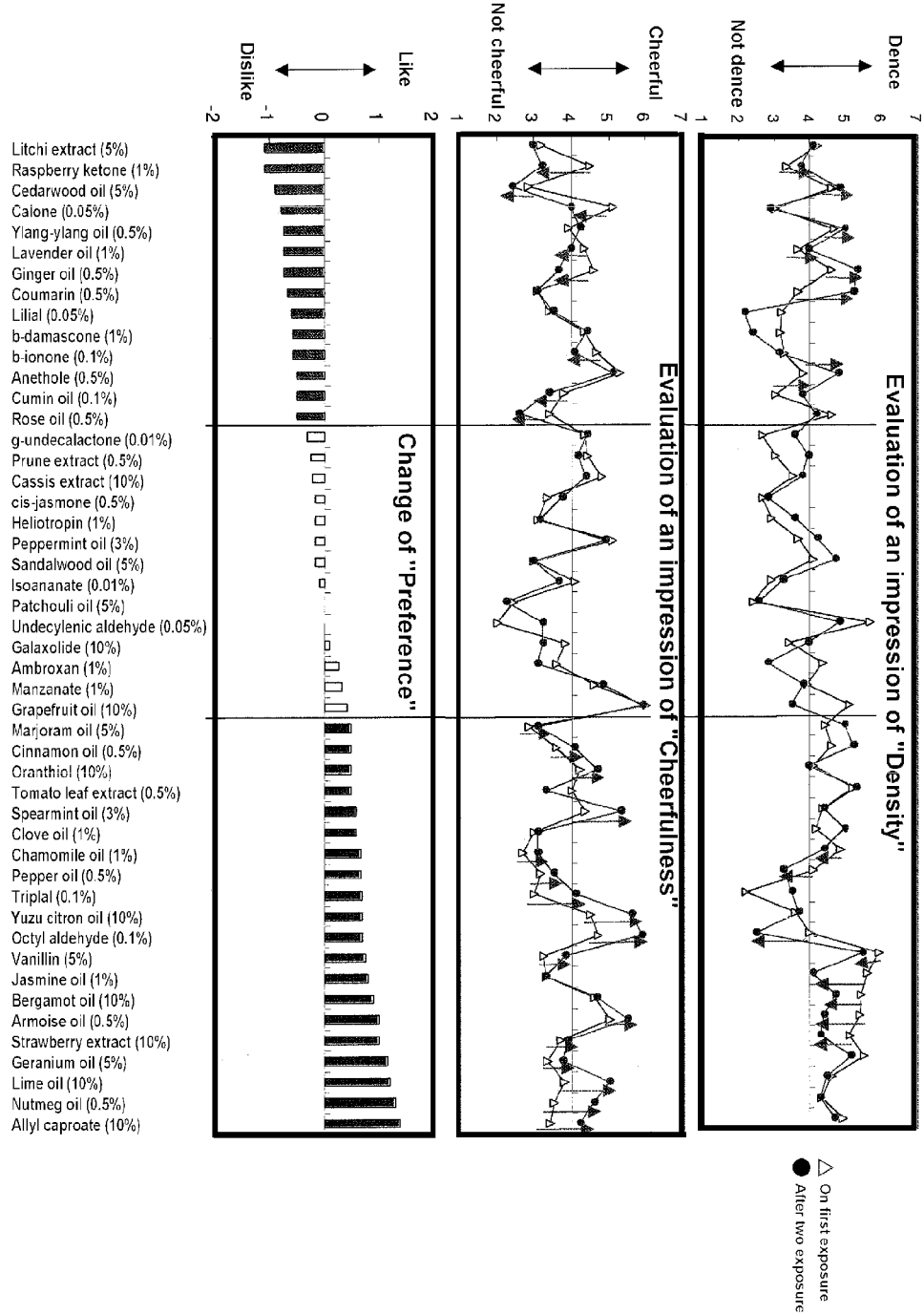
FIG. 4 is a diagram summarizing change in preferences for various perfume ingredients by continuous use and evaluation results of impressions of "density" and "cheerfulness" on first exposure and after two exposures.

As seen in Tables 7 and 8 above and FIG. 4, in a perfume ingredient that enhances a preference therefor by continuous use, it was revealed that an impression of the "density" thereof is evaluated as being reduced by continuous use, or an impression of the "cheerfulness" thereof is evaluated as being needs to be evaluated as being increased by continuous use to give a perfume ingredient that enhances a preference therefor by continuous use.

Subsequently, the present inventors classified the 48 perfume ingredients known in the art into three groups, (1) a reduction by 0.5 or more, (2) a change less than 0.5, and (3) an increase by 0.5 or more, in terms of change in preferences between on first exposure and after two exposures. And the present inventors conducted further detailed study on the relationship between change in preference by continuous use and an evaluation of an impression of the "density" on first exposure by making a comparison on an average value of evaluation results of an impression of "density" in each group on first exposure. The evaluation results are summarized and shown in Table 9 below and FIG. 5.

TABLE 9

| Group | Evaluation of impression of "density" (on first exposure) |
|---|---|
| 1: reduction in preference By 0.5 or more | 3.8 |
| 2: change in preference less than 0.5 | 3.6 |
| 3: increase in preference By 0.5 or more | 4.6 |

Figure 5:
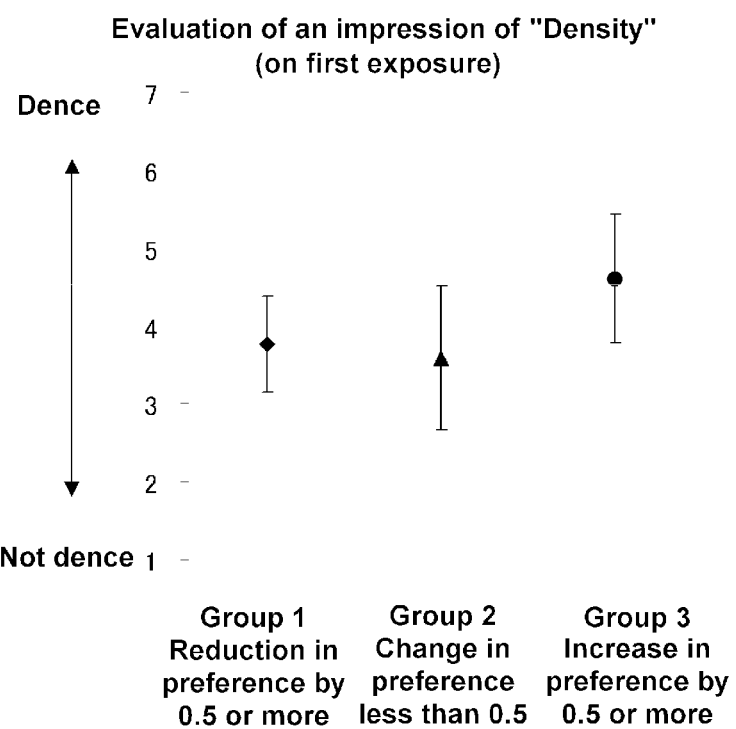
FIG. 5 is a diagram summarizing an average value of evaluation results of an impression of "density" in each group on first exposure by classifying various perfume ingredients into 3 groups, (1) a reduction by 0.5 or more, (2) a change less than 0.5, and (3) an increase by 0.5 or more, in terms of change in preferences therefor on first exposure and after two exposures.

Table 9 above and FIG. 5 demonstrated that an impression of the "density" of a perfume ingredient that enhances a preference therefor by continuous use tends to be evaluated as being high on first exposure. By contrast, it was shown that an impression of the "density" of a perfume ingredient that reduces a preference therefor by continuous use and an impression of the "density" of a perfume ingredient that exhibits no change in preference by continuous use tend to be evaluated as being low on first exposure. From these results, for selecting a perfume ingredient that enhances a preference therefor by continuous use, it is particularly preferred that a perfume ingredient whose impression of the "density" on first exposure is rated 4 or higher should be selected.

Relationship Between Overall Fragrance Note of Perfume Composition and Evaluations of Impressions of "Density" and "Cheerfulness"

In the test above, the single perfume ingredient was used to examine the relationship between change in preference by continuous use and evaluations of impressions of "density" and "cheerfulness". The present inventors also studied whether this relationship can be applied to the overall fragrance note of a perfume composition and therefore conducted the same evaluations as in the test above by use of prepared perfumes whose fragrances were formulated in advance. The results are shown in Table 10 below and FIG. 6.

TABLE 10

| Prepared perfume | Preference (first) | Preference (twice) | "Density" (first) | "Density" (twice) | "Cheerfulness" (first) | "Cheerfulness" (twice) |
|---|---|---|---|---|---|---|
| 1 | 4.8 | 3.1 | 4.3 | 4.8 | 4.3 | 3.4 |
| 2 | 5.3 | 3.7 | 3.9 | 4.3 | 4.9 | 4.7 |
| 3 | 4.1 | 3.1 | 4.1 | 5.1 | 5.0 | 3.7 |
| 4 | 5.0 | 4.1 | 4.1 | 4.4 | 4.3 | 4.3 |
| 5 | 4.9 | 4.1 | 3.0 | 4.2 | 4.8 | 4.2 |
| 6 | 5.9 | 5.1 | 2.0 | 2.6 | 5.6 | 5.3 |
| 7 | 3.5 | 3.0 | 5.1 | 5.6 | 3.1 | 4.1 |
| 8 | 4.3 | 3.9 | 4.1 | 3.3 | 4.5 | 4.2 |
| 9 | 4.7 | 4.3 | 3.5 | 4.2 | 5.1 | 4.4 |
| 10 | 5.1 | 4.7 | 4.2 | 4.6 | 5.7 | 5.6 |
| 11 | 5.5 | 5.2 | 4.1 | 4.0 | 5.7 | 5.4 |
| 12 | 3.1 | 2.8 | 4.7 | 4.2 | 3.8 | 2.9 |
| 13 | 3.7 | 3.6 | 3.9 | 3.8 | 4.3 | 3.8 |
| 14 | 4.5 | 4.4 | 3.6 | 4.0 | 4.4 | 4.6 |
| 15 | 4.3 | 4.3 | 3.3 | 3.7 | 4.3 | 3.7 |
| 16 | 3.4 | 3.5 | 3.7 | 5.5 | 3.9 | 3.7 |
| 17 | 2.2 | 2.3 | 4.8 | 4.0 | 3.0 | 3.1 |
| 18 | 3.9 | 4.0 | 5.0 | 4.3 | 5.3 | 4.6 |
| 19 | 3.8 | 4.1 | 3.6 | 4.2 | 3.8 | 4.2 |
| 20 | 5.3 | 5.9 | 4.2 | 4.7 | 5.4 | 5.5 |
| 21 | 3.6 | 4.3 | 4.9 | 4.1 | 4.7 | 5.0 |
| 22 | 2.4 | 3.6 | 5.0 | 4.1 | 3.6 | 4.0 |
| 23 | 1.8 | 3.0 | 5.6 | 4.9 | 2.5 | 3.8 |
| 24 | 1.9 | 3.6 | 5.6 | 4.5 | 3.0 | 4.3 |

Figure 6:
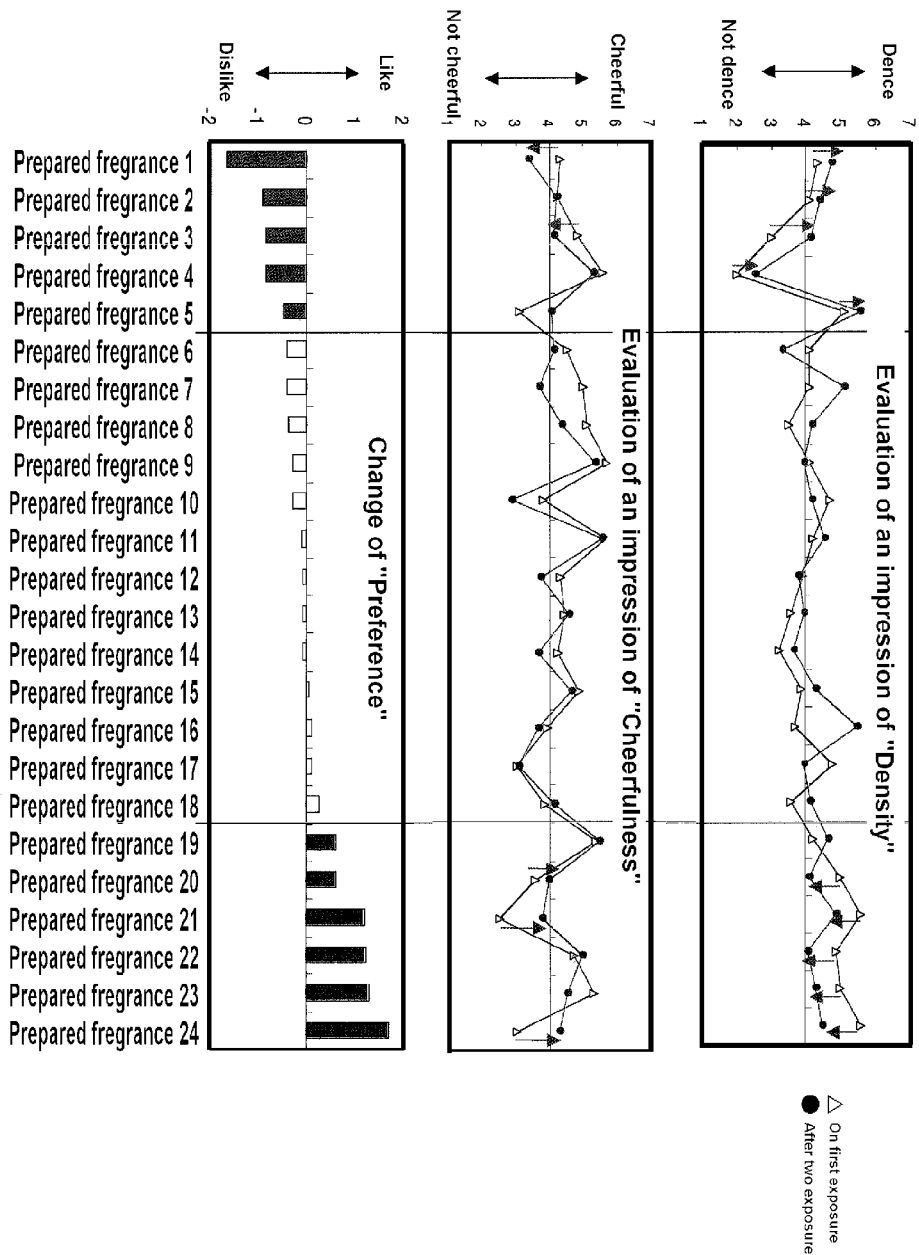
FIG. 6 is a diagram summarizing change in preferences for various prepared perfumes by continuous use and evaluation results of impressions of "density" and "cheerfulness" on first exposure and after two exposures.

Table 10 above and FIG. 6 demonstrated that, as in the evaluations on the single perfume ingredient, in a prepared perfume that enhances a preference therefor by continuous use, an impression of the "density" thereof is evaluated as being reduced by continuous use, whereas an impression of the "cheerfulness" thereof is evaluated as being increased by continuous use. Moreover, it was shown that, particularly, a prepared perfume that significantly enhances a preference therefor by continuous use needs to increase an impression of the "density" thereof on first exposure.

From these results, it was shown that a perfume composition that enhances a preference therefor by continuous use can be obtained by formulating the fragrance of the perfume composition so that an impression of the "density" thereof is evaluated as being reduced by continuous use and that an impression of the "cheerfulness" thereof is evaluated as being increased by continuous use. Moreover, it was shown that for significantly enhancing a preference for a perfume composition by continuous use, it is preferred that a fragrance should be formulated so that an impression of the "density" thereof on first exposure is rated 4 or higher.

Formula examples of prepared perfumes actually prepared by the present inventors based on these findings will be shown below.

TABLE 11

| Prepared perfume formula 1 | |
|---|---|
| Name of perfume ingredient | % by mass |
| Manzanate | 5 |
| Limonene | 10 |
| Prenyl acetate | 5 |
| Hexyl acetate | 3 |

TABLE 11-continued

Prepared perfume formula 1

| Name of perfume ingredient | % by mass |
|---|---|
| cis-3-hexenyl acetate | 2 |
| Rose oxide | 0.25 |
| Allyl caproate | 0.2 |
| p-cresyl methyl ether | 3 |
| Allyl heptoate | 1 |
| cis-3-hexenyl methyl carbonate | 0.6 |
| Isocyclocitral | 0.7 |
| Linalool | 3 |
| Benzaldehyde | 1 |
| Linalyl acetate | 3 |
| Cyclohexanemethanol α,3,3-trimethyl formate | 1 |
| Ethyl 2-cyclohexylpropionate | 1 |
| o-t-butylcyclohexanyl acetate | 4 |
| β-caryophyllene | 1 |
| Ethyl safranate | 2 |
| Citronellyl acetate | 0.5 |
| Ethyl(2-methyl-1,3-dioxiran-2-yl) acetate | 0.2 |
| Styralyl acetate | 2 |
| Neryl acetate | 0.1 |
| Benzyl acetate | 6 |
| Geranyl acetate | 1 |
| Citronellol | 2 |
| Dimethylbenzylcarbinyl acetate | 2 |
| Ethyltricyclo[5.2.1.0$^{2.6}$]decane-2-carboxylate | 2 |
| Damascenone | 0 |
| γ-methylionone | 6 |
| Dimethylbenzylcarbinyl n-butyrate | 1 |
| Phenylethyl alcohol | 2 |
| 6,7-dihydro-1,1,2,3,3-pentamethyl-4(5H)-indanone | 1 |
| β-ionone | 3 |
| Tricyclodecenyl acetate | 0.3 |
| β-n-methylionone | 0.2 |
| Lilial | 1.5 |
| 7-acetyl-1,2,3,4,5,6,7,8-octahydro-1,1,6,7-tetramethylnaphthalene | 1 |
| Hexyl salicylate | 0.5 |
| Methyl dihydrojasmonate | 5 |
| Vanillin | 0.2 |
| Ethyl maltol | 0.05 |
| Galaxolide | 5 |
| Tonalid | 5 |
| Dipropylene glycol | 5.08 |
| Total | 100.0 |

Subsequently, the present inventors prepared a cosmetic (shampoo) blended with the prepared perfume formula 1 and evaluated change in preference for the cosmetic by continuous use. The formula of the cosmetic is shown in Table 12 below. Moreover, details of the test and evaluation criteria are shown below. The results are shown in Table 13 below and FIG. 7.

TABLE 12

Cosmetic formula 1 (shampoo)

| | % by mass |
|---|---|
| Water | Balance |
| Sodium polyoxyethylene lauryl ether sulfate | 9.7 |
| Coconut oil fatty acid methyltaurine sodium | 3.6 |
| 2-alkyl(11-17)-N-carboxymethyl-N-hydroxyethylimidazolinium betaine | 3 |
| Coconut oil fatty acid amidopropyl betaine | 3 |
| Glycol distearate | 2.5 |
| Dipropylene glycol | 2.4 |
| Coconut oil fatty acid monoethanolamide | 2 |
| Sorbitol | 1.4 |
| Sodium chloride | 0.6 |
| Dimethyldiallylammonium chloride/acrylamide copolymer | 0.04 |
| Dimethylpolysiloxane | 0.6 |
| Citric acid | 0.4 |
| Locust bean gum/hydroxypropyltrimethylammonium ether chloride | 0.4 |
| Disodium edetate | 0.05 |
| Sodium benzoate | 0.3 |
| Methylparaben | q.s. |
| Propylparaben | q.s. |
| Prepared perfume formula 1 | 0.5 |
| Total | 100.0 |

Details of Test 36 panelists actually used the cosmetic formula 1 (shampoo) consecutively for 4 weeks and evaluated it on a scale of 1 to 7 for each of a "preference for a fragrance", "a sense of satisfaction with a product", and an "intention to continuously use a product" each time in first use (first day) and after four-week consecutive use (after four weeks) according to evaluation criteria below.

Evaluation Criteria
"Preference for fragrance"
Very like
Like
Moderately like
Neither like nor dislike
Moderately dislike
Dislike
Very dislike
"Sense of satisfaction with whole product"
Very satisfied
Satisfied
Moderately satisfied
Neither satisfied nor unsatisfied
Moderately unsatisfied
Unsatisfied
Very unsatisfied
"Intention to continuously use product"
Strongly have intention
Have intention
Slightly have intention
Neither have intention nor have no intention
Slightly have no intention
Have no intention
Absolutely have no intention

TABLE 13

| | | First day | After four weeks |
|---|---|---|---|
| Preference for fragrance | Very like | 3 (8%) | 7 (19%) |
| | Like | 11 (31%) | 9 (25%) |
| | Moderately like | 4 (11%) | 9 (25%) |
| | Neither like nor dislike | 12 (33%) | 5 (14%) |
| | Moderately dislike | 5 (14%) | 4 (11%) |
| | Dislike | 1 (3%) | 0 (0%) |
| | Very dislike | 0 (0%) | 2 (6%) |
| Sense of satisfaction with whole product | Very satisfied | 2 (6%) | 6 (17%) |
| | Satisfied | 14 (39%) | 15 (42%) |
| | Moderately satisfied | 11 (31%) | 9 (25%) |
| | Neither satisfied nor unsatisfied | 7 (19%) | 4 (11%) |
| | Moderately unsatisfied | 1 (3%) | 2 (6%) |
| | Unsatisfied | 1 (3%) | 0 (0%) |
| | Very unsatisfied | 0 (0%) | 0 (0%) |
| Intention to continuously use | Strongly have intention | 2 (6%) | 6 (17%) |
| | Have intention | 10 (28%) | 14 (39%) |

TABLE 13-continued

|  | | First day | After four weeks |
|---|---|---|---|
| product | Slightly have intention | 11 (31%) | 6 (17%) |
|  | Neither have intention nor have no intention | 12 (33%) | 6 (17%) |
|  | Slightly have no intention | 1 (3%) | 2 (6%) |
|  | Have no intention | 0 (0%) | 1 (3%) |
|  | Absolutely have no intention | 0 (0%) | 1 (3%) |

Figure 7:
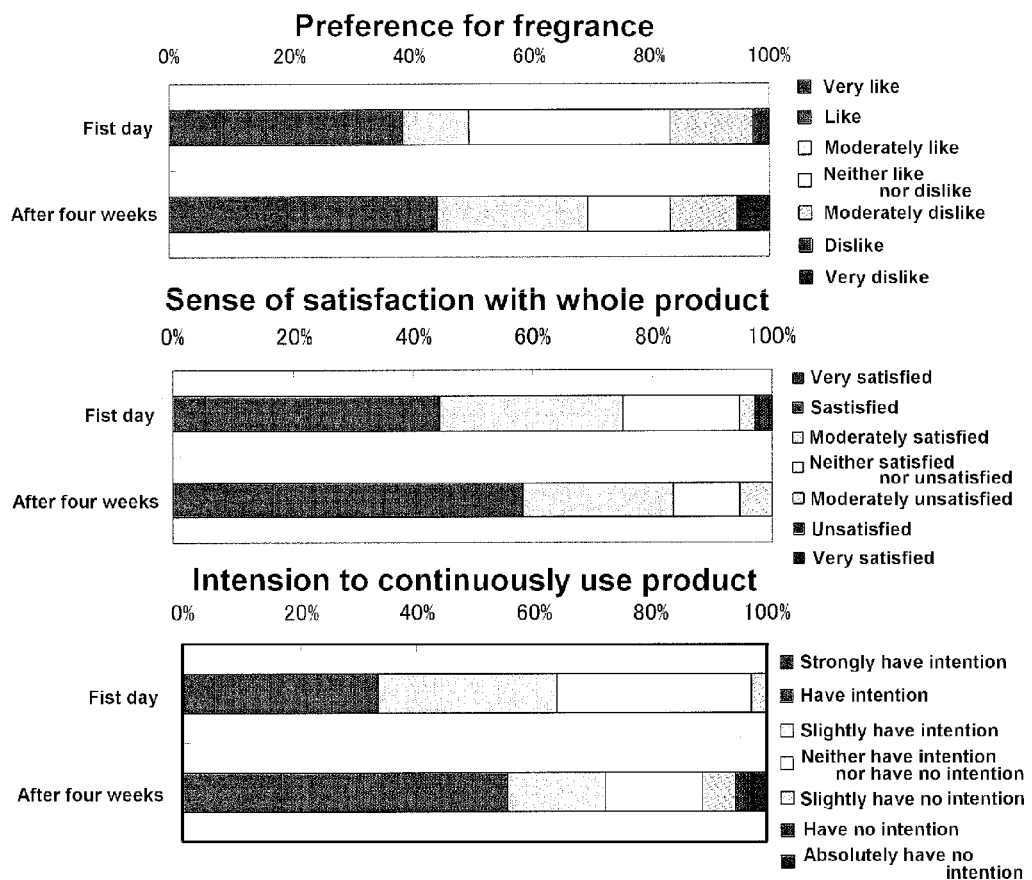
FIG. 7 is a diagram summarizing evaluation results of a "preference for a fragrance", "a sense of satisfaction with a product", and an "intention to continuously use a product" in a cosmetic (shampoo) blended with the prepared perfume of the present invention each time in first use (first day) and after four-week consecutive use (after four weeks)

Table 13 above and FIG. 7 demonstrated that the cosmetic blended with the prepared perfume whose fragrance is formulated by the preparation method according to the present invention is evaluated as being somewhat high in the "preference for a fragrance", the "sense of satisfaction with the whole product", and the "intention to continuously use a product" in first use and evaluated as being improved in all of the evaluation items after 4-week consecutive use as compared with in first use.

From these results, it was confirmed that the prepared perfume of the present invention can be formulated into a cosmetic to obtain a cosmetic that can give an excellent preference therefor in first use and enhance evaluation results of the preference and so on by repetitive and consecutive use.

Example 2

Next, an evaluation test was conducted on the use texture of a hair cleanser.

Evaluation of Use Texture of Hair Cleanser (on First Day and after Five Days)

106 panelists used shampoos prepared according to composition shown in Table 14 below (Example 2 and Comparative Example 1) consecutively for five days and evaluated them on a scale of 1 to 5 for each of a "degree of foaming", "fineness of foam", a "capability of finger combing during foaming", a "degree of reduced creaky feeling of hair during rinsing", a "capability of finger combing during rinsing", a "capability of finger combing after rinsing", "softness of hair after rinsing", and a "capability of washing off the dirt of hair/cleanliness" each time in first use (first day) and after five-day consecutive use (after five days) according to evaluation criteria. In this context, a value obtained by dividing, by the number of the panelists, the total sum of the scores given by the panelists is used as each evaluation value.

The prepared perfume formula 1 was adopted as an ingredient (iv) in Example 2. An ingredient (iv) in Comparative Example 1 is shown in Table 15 below.

| <Evaluation criteria> | |
|---|---|
| Very good | 5 |
| Good | 4 |
| Neither good nor poor | 3 |
| Poor | 2 |
| Very poor | 1 |

TABLE 14

|  | Example 2 | Comparative Example 1 |
|---|---|---|
| (i) | | |
| 2-alkyl(11-17)-N-carboxymethyl-N-hydroxyethylimidazolinium betaine | 3 | 3 |
| Coconut oil fatty acid amidopropyl betaine | 3 | 3 |
| (ii) | | |
| Locust bean gum/hydroxypropyltrimethylammonium ether chloride | 0.4 | 0.4 |
| Dimethyldiallylammonium chloride/acrylamide copolymer | 0.04 | 0.04 |
| (iii) | | |
| Coconut oil fatty acid methyltaurine sodium | 3.6 | 3.6 |
| (iv) | | |
| Prepared perfume formula 1 | 0.5 | — |
| Comparative formula 1 | — | 0.5 |
| Sodium polyoxyethylene lauryl ether sulfate | 9.7 | 9.7 |
| Glycol distearate | 2.5 | 2.5 |
| Dipropylene glycol | 2.4 | 2.4 |
| Coconut oil fatty acid monoethanolamide | 2 | 2 |
| Sorbitol | 1.4 | 1.4 |
| Sodium chloride | 0.6 | 0.6 |
| Dimethylpolysiloxane | 0.6 | 0.6 |
| Citric acid | 0.4 | 0.4 |
| Disodium edetate | 0.05 | 0.05 |
| Sodium benzoate | 0.3 | 0.3 |
| Methylparaben | q.s. | q.s. |
| Propylparaben | q.s. | q.s. |
| Water | Balance | Balance |
| First day | | |
| Degree of foaming | 4.1 | 4.1 |
| Fineness of foam | 3.9 | 3.8 |
| Capability of finger combing during foaming | 3.9 | 3.8 |
| Degree of reduced creaky feeling of hair during rinsing | 3.6 | 3.7 |
| Capability of finger combing during rinsing | 3.6 | 3.7 |
| Capability of finger combing after rinsing | 3.4 | 3.5 |
| Softness of hair after rinsing | 3.4 | 3.2 |
| Capability of washing off dirt of hair/cleanliness | 3.6 | 3.6 |
| After five days | | |
| Degree of foaming | 4.5 | 4.4 |
| Fineness of foam | 4.2 | 4.2 |
| Capability of finger combing during foaming | 4.2 | 4.0 |
| Degree of reduced creaky feeling of hair during rinsing | 3.9 | 3.6 |
| Capability of finger combing during rinsing | 3.8 | 3.5 |
| Capability of finger combing after rinsing | 3.7 | 3.3 |
| Softness of hair after rinsing | 3.6 | 3.3 |
| Capability of washing off dirt of hair/cleanliness | 3.7 | 3.8 |

TABLE 15

| Comparative formula 1 | |
|---|---|
| Name of ingredient | % by mass |
| Lemon oil | 3 |
| Limonene | 2 |
| cis-3-hexyl acetate | 0.3 |
| cis-3-hexenol | 0.2 |
| iso-amyl acetate | 0.2 |
| Linalool | 5 |
| Linalyl acetate | 10 |
| Citronellyl acetate | 2 |
| Benzyl acetate | 2 |
| Geranyl acetate | 1 |
| Citronellol | 3 |
| Geraniol | 2 |
| Florosa | 5 |
| Dipropylene glycol | 18.3 |
| Phenyl ethyl alcohol | 3 |
| Lilial | 5 |

TABLE 15-continued

Comparative formula 1

| Name of ingredient | % by mass |
|---|---|
| 7-acetyl-1,2,3,4,5,6,7,8-octahydro-1,1,6,7-tetramethylnaphthalene | 5 |
| Methyl dihydrojasmonate | 20 |
| α-hexyl cinnamic aldehyde | 10 |
| Pentalid | 3 |
| Total | 100.0 |

Figure 8:
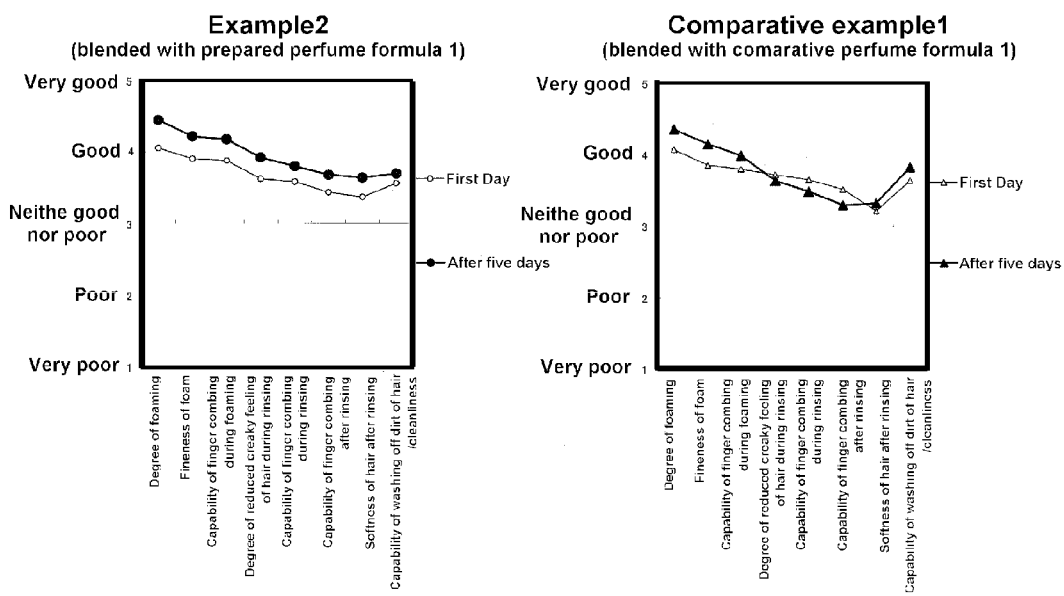
FIG. 8 is a diagram summarizing evaluation results of various items of use texture of two hair cleansers according to Example of the present invention and Comparative Example (Example 2: blended with prepared perfume formula 1; Comparative Example 1: blended with comparative formula 1) each time in first use (first day) and after five-day consecutive use (after five days).

As shown in Table 14 and FIG. 8, it was demonstrated that the shampoo of Example 2 blended with the prepared perfume formula 1 containing manzanate, allyl caproate, vanillin, and galaxolide as the ingredients (iv) was evaluated as being improved in all of the various evaluation items of the use texture thereof after five-day consecutive use as compared with on the first day. By contrast, the shampoo of Comparative Example 1 blended with the comparative formula 1 free of these various ingredients (iv) was evaluated as being either improved or reduced depending on the evaluation items after consecutive use as compared with on the first day. Thus, it cannot be said that the shampoo of Comparative Example 1 was evaluated as being improved in all of the evaluation items of use texture after consecutive use.

Moreover, the present inventors conducted further detailed study. As a result, it was confirmed that the following ingredients can be formulated into a shampoo to thereby improve use texture thereof in consecutive use: galaxolide, ambroxan, manzanate, grapefruit oil, marjoram oil, cinnamon oil, aurantiol, tomato leaf extract, spearmint oil, clove oil, chamomile oil, pepper oil, Triplal, Yuzu citron (Citrus junos) oil, octylaldehyde, vanillin, jasmine oil, bergamot oil, armoise oil, strawberry extract, geranium oil, lime oil, nutmeg oil, and allyl caproate.

Example 3

TABLE 16

Example 3 Shampoo

| | % by mass |
|---|---|
| Water | Balance |
| Sodium polyoxyethylene lauryl ether sulfate | 7 |
| Coconut oil fatty acid methyltaurine sodium | 5.5 |
| Coconut oil fatty acid amidopropyl betaine | 4.8 |
| Dipropylene glycol | 1.6 |
| Glycol distearate | 1.5 |
| Sorbitol | 1.4 |
| Propylene glycol monolaurate | 1.4 |
| Sodium chloride | 0.9 |
| Guar gum/hydroxypropyltrimethylammonium ether chloride | 0.3 |
| (bis-isobutyl PEG-14/amodimethicone) copolymer | 0.5 |
| Hydroxyethylcellulose/hydroxypropyltrimethylammonium chloride ether | 0.1 |
| Citric acid | 0.2 |
| Disodium edetate | 0.1 |
| Sodium benzoate | 0.3 |
| Phenoxy ethanol | q.s. |
| Methylparaben | q.s. |
| Prepared perfume formula 1 | 0.5 |
| Total | 100.0 |

The shampoo of Example 3 offers excellent use texture and improves evaluation results of the use texture by repetitive and consecutive use.

Hereinafter, the present invention will be described more specifically with another Example. However, the present invention is not limited to this Example.

Example 4

TABLE 17

Prepared perfume formula 2

| Name of perfume ingredient | % by mass |
|---|---|
| α-pinene | 0.1 |
| β-pinene | 2 |
| Limonene | 18 |
| γ-terpinene | 1 |
| p-cymene | 1 |
| Allyl caproate | 7 |
| 1-tetradecene | 0.2 |
| 2,2,5-trimethyl-5-pentyl-cyclopentanone | 0.2 |
| Linalool | 2 |
| Linalyl acetate | 3 |
| α-bergamotene | 0.2 |
| Ethyl linalool | 5 |
| Menthol | 8 |
| α-terpinol | 1 |
| Neryl acetate | 0.5 |
| β-bisabolene | 0.2 |
| Benzyl acetate | 4 |
| Geranyl acetate | 0.6 |
| Citronellol | 5 |
| Florosa | 3 |
| Dimethylbenzylcarbinyl acetate | 0.5 |
| Geraniol | 2 |
| γ-methylionone | 3 |
| Dimethylbenzylcarbinyl n-butyrate | 1 |
| α-n-methylionone | 0.3 |
| Cyclamen aldehyde | 4 |
| Lilial | 6 |
| Hexyl salicylate | 0.5 |
| Methyl cedryl ketone | 2 |
| cis-3-hexyl salicylate | 0.5 |
| Methyl dihydrojasmonate | 5 |
| Hexyl cinnamic aldehyde | 2 |
| α-methyl-3,4-(methylenedioxy) hydrocinnamaldehyde | 0.3 |
| Galaxolide | 3 |
| Dipropylene glycol | 9.4 |
| Total | 100.0 |

TABLE 18

Prepared perfume formula 3

| Name of perfume ingredient | % by mass |
|---|---|
| β-pinene | 2 |
| Myrcene | 4 |
| Limonene | 30 |
| γ-terpinene | 2 |
| p-cymene | 3 |
| 6-methylheptenone | 0.2 |
| Allyl caproate | 10 |
| 2,2,5-trimethyl-5-pentyl-cyclopentanone | 5 |
| Benzaldehyde | 0.2 |
| Linalyl acetate | 5 |
| Ethyl linalool | 2 |
| Menthol | 2 |
| Citral | 0.2 |
| α-terpineol | 1 |
| Terpinyl acetate | 0.1 |
| Benzyl acetate | 2 |
| Geranyl acetate | 0.3 |
| Citronellol | 0.3 |
| Florosa | 3 |
| Dimethylbenzylcarbinyl acetate | 0.3 |
| α-damascone | 0.2 |

TABLE 18-continued

Prepared perfume formula 3

| Name of perfume ingredient | % by mass |
|---|---|
| γ-methylionone | 3 |
| β-ionone | 1 |
| Cyclamen aldehyde | 1 |
| Lilial | 5 |
| Galaxolide | 3 |
| Dipropylene glycol | 15.7 |
| Total | 100.0 |

TABLE 19

Cosmetic formula 2 (shampoo)

| | % by mass |
|---|---|
| Water | Balance |
| Sodium polyoxyethylene lauryl ether sulfate | 7 |
| Coconut oil fatty acid methyltaurine sodium | 5.5 |
| Coconut oil fatty acid amidopropyl betaine | 4.8 |
| Dipropylene glycol | 1.6 |
| Glycol distearate | 1.5 |
| Sorbitol | 1.4 |
| Propylene glycol monolaurate | 1.4 |
| Sodium chloride | 0.9 |
| Guar gum/hydroxypropyltrimethylammonium ether chloride | 0.3 |
| Hydroxyethylcellulose/hydroxypropyltrimethylammonium chloride ether | 0.1 |
| Citric acid | 0.2 |
| Disodium edetate | 0.1 |
| Sodium benzoate | 0.3 |
| Phenoxy ethanol | q.s. |
| Methylparaben | q.s. |
| Prepared perfume formula 1 | 0.5 |
| Total | 100.0 |

TABLE 20

Cosmetic formula 3 (conditioner)

| | % by mass |
|---|---|
| Water | Balance |
| Sorbitol | 7 |
| Dipropylene glycol | 5 |
| Stearyl alcohol | 5 |
| Dimethylpolysiloxane | 2.2 |
| Propylene glycol dimethylamine stearate | 1.4 |
| Glutamic acid | 0.6 |
| Hydroxyethyl urea | 0.3 |
| Aminoethylaminopropylmethylsiloxane/dimethylsiloxane copolymer | 0.2 |
| Polyethylene glycol-90 M | 0.05 |
| Mineral oil | 0.5 |
| Phenoxy ethanol | q.s. |
| Prepared perfume formula 1 | 0.5 |
| Total | 100.0 |

TABLE 21

Cosmetic formula 4 (conditioner)

| | % by mass |
|---|---|
| Water | Balance |
| Isopentyldiol | 4 |
| Sorbitol | 4 |
| Dimethylpolysiloxane | 4 |

TABLE 21-continued

Cosmetic formula 4 (conditioner)

| | % by mass |
|---|---|
| Stearyl alcohol | 2.5 |
| Behenyl alcohol | 2.2 |
| Stearyltrimethylammonium chloride | 2 |
| 2-ethylhexyl palmitate | 1 |
| Aminoethylaminopropylmethylsiloxane/dimethylsiloxane copolymer | 0.15 |
| Polyethylene glycol-90 M | 0.03 |
| Sodium citrate | 0.05 |
| Phenoxy ethanol | q.s. |
| Methylparaben | q.s. |
| Prepared perfume formula 1 | 0.5 |
| Total | 100.0 |

TABLE 22

Cosmetic formula 5 (treatment)

| | % by mass |
|---|---|
| Water | Balance |
| Sorbitol | 21 |
| Dimethylpolysiloxane | 7 |
| Hydrogenated rapeseed alcohol | 6 |
| Isopentyldiol | 5 |
| Behenyltrimethylammonium chloride | 3 |
| Aminoethylaminopropylmethylsiloxane/dimethylsiloxane copolymer | 0.7 |
| Alkyl(C12,14)oxyhydroxypropyl arginine HCl | 0.4 |
| Glutamic acid | 0.25 |
| Polyethylene glycol-90 M | 0.02 |
| 2-ethylhexyl palmitate | 0.6 |
| Sodium benzoate | 0.3 |
| Phenoxy ethanol | q.s. |
| Prepared perfume formula 1 | 0.5 |
| Total | 100.0 |

TABLE 23

Cosmetic formula 6 (treatment)

| | % by mass |
|---|---|
| Water | Balance |
| Isopentyldiol | 5 |
| Dimethylpolysiloxane | 5 |
| Sorbitol | 4 |
| Cetanol | 4 |
| Behenyltrimethylammonium chloride | 2 |
| Mineral oil | 2 |
| Behenyl alcohol | 1.4 |
| Aminoethylaminopropylmethylsiloxane/dimethylsiloxane copolymer | 0.5 |
| Stearyltrimethylammonium chloride | 0.1 |
| Polyethylene glycol-90 M | 0.03 |
| Phenoxy ethanol | q.s. |
| Methylparaben | q.s. |
| Prepared perfume formula 1 | 0.5 |
| Total | 100.0 |

TABLE 24

Cosmetic formula 7 (treatment)

| | % by mass |
|---|---|
| Water | Balance |
| Butylene glycol | 20 |
| Dimethylpolysiloxane | 9 |
| Hydrogenated rapeseed alcohol | 7 |
| Behenyltrimethylammonium chloride | 3 |
| Sorbitol | 1.4 |
| Aminoethylaminopropylmethylsiloxane/dimethylsiloxane copolymer | 0.7 |
| Lecithin | 0.2 |
| Polyethylene glycol-90 M | 0.03 |
| Glyceryl oleate | 0.8 |
| Phenoxy ethanol | q.s. |
| Methylparaben | q.s. |
| Prepared perfume formula 1 | 0.5 |
| Total | 100.0 |

TABLE 25

Cosmetic formula 8 (skin lotion)

| | % by mass |
|---|---|
| Water | Balance |
| Ethanol | 2 |
| Glycerin | 5 |
| Dipropylene glycol | 5 |
| 1,3-butylene glycol | 6 |
| Polyoxyethylene (14) polyoxypropylene (7) dimethyl ether | 2 |
| Sodium alginate | 0.1 |
| Polyoxyethylene (2) alkyl (12-16) ether phosphate | 0.3 |
| Polyglyceryl diisostearate | 0.3 |
| Glyceryl tri-2-ethylhexanoate | 0.15 |
| Yeast extract | 0.1 |
| *Sophora flavescens* extract | 0.05 |
| Collagen | 0.1 |
| Elastin | 0.1 |
| Citric acid | 0.02 |
| Sodium citrate | 0.08 |
| Disodium edetate | 0.03 |
| Phenoxy ethanol | q.s. |
| Prepared perfume formula 2 | 0.03 |
| Total | 100.0 |

TABLE 26

Cosmetic formula 9 (cleansing foam)

| | % by mass |
|---|---|
| Water | Balance |
| Myristic acid | 15 |
| Lauric acid | 5 |
| Stearic acid | 12 |
| Glycerin | 15 |
| Potassium hydroxide | 6 |
| Sorbitol | 6 |
| Dipropylene glycol | 5 |
| Polyethylene glycol-30 | 5 |

TABLE 26-continued

Cosmetic formula 9 (cleansing foam)

| | % by mass |
|---|---|
| Polyoxyethylene (60) glyceryl isostearate | 3 |
| Glycol distearate | 1 |
| Self-emulsifying glyceryl stearate | 1 |
| Coconut oil fatty acid methyltaurine sodium | 0.3 |
| Disodium edetate | 0.1 |
| Phenoxy ethanol | q.s. |
| Prepared perfume formula 3 | 0.2 |
| Total | 100.0 |

All of the cosmetic formulas 2 to 9 blended with the prepared perfume formulas 1 to 3 obtained by the method for formulating a fragrance according to the present invention give a high preference therefor in first use and enhances evaluation results of the preference, usability, and so on by repetitive and consecutive use.

What is claimed is:

1. A method for enhancing a preference for a product by repetitive use comprising formulating a perfume composition into the product, wherein the perfume composition consists of (I) allyl caproate and (II) ambroxan or geranium oil.

2. The method of claim 1, further comprising exposing a subject to a vapor from the product by the repetitive use of the product, thereby enhancing a preference for the product, the vapor consisting of (I) allyl caproate and (II) ambroxan or geranium oil.

3. The method of claim 1, further comprising exposing a subject to a vapor from the product two or more times, thereby enhancing a preference for the product by repetitive use, the vapor consisting of (I) allyl caproate and (II) ambroxan or geranium oil.

4. A method for enhancing a preference for a product by repetitive use comprising formulating a perfume composition into the product, wherein the perfume composition consists of (I) allyl caproate and (II) geranium oil.

5. A method for enhancing a preference for a product by repetitive use comprising formulating a perfume composition into the product, wherein the perfume composition consists of (I) allyl caproate and (II) ambroxan.

6. The method of claim 4, further comprising exposing a subject to a vapor from the product by the repetitive use of the product, thereby enhancing a preference for the product, the vapor consisting of (I) allyl caproate and (II) geranium oil.

7. The method of claim 4, further comprising exposing a subject to a vapor from the product two or more times, thereby enhancing a preference for the product by repetitive use, the vapor consisting of (I) allyl caproate and (II) geranium oil.

8. The method of claim 5, further comprising exposing a subject to a vapor from the product by the repetitive use of the product, thereby enhancing a preference for the product, the vapor consisting of (I) allyl caproate and (II) ambroxan.

9. The method of claim 5, further comprising exposing a subject to a vapor from the product two or more times, thereby enhancing a preference for the product by repetitive use, the vapor consisting of (I) allyl caproate and (II) ambroxan.

* * * * *